(12) United States Patent
Samuel et al.

(10) Patent No.: US 8,722,410 B2
(45) Date of Patent: *May 13, 2014

(54) METHODS FOR TRANSFERRING MOLECULAR SUBSTANCES INTO PLANT CELLS

(75) Inventors: Jayakumar P. Samuel, Carmel, IN (US); Frank Burroughs, Noblesville, IN (US); Suraj Dixit, Bloomington, IN (US); Mark W. Zettler, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 491 days.

This patent is subject to a terminal disclaimer.

(21) Appl. No.: 12/245,685

(22) Filed: Oct. 3, 2008

(65) Prior Publication Data

US 2009/0104700 A1 Apr. 23, 2009

Related U.S. Application Data

(60) Provisional application No. 60/978,059, filed on Oct. 5, 2007.

(51) Int. Cl.
| | | |
|---|---|---|
| *C12N 15/87* | (2006.01) | |
| *A01H 5/10* | (2006.01) | |
| *B82Y 5/00* | (2011.01) | |
| *B82Y 30/00* | (2011.01) | |
| *B82Y 10/00* | (2011.01) | |

(52) U.S. Cl.
USPC ........ 435/470; 800/293; 800/320.1; 800/279; 977/705; 977/714; 977/774; 977/728; 435/430.1

(58) Field of Classification Search
None
See application file for complete search history.

(56) References Cited

U.S. PATENT DOCUMENTS

| 4,769,061 A | 9/1988 | Comai |
|---|---|---|
| 4,810,648 A | 3/1989 | Stalker |
| 4,940,835 A * | 7/1990 | Shah et al. .................. 800/288 |
| 4,975,374 A | 12/1990 | Goodman et al. |
| 5,266,317 A | 11/1993 | Tomalski et al. |
| 5,494,813 A | 2/1996 | Hepher et al. |
| 6,248,876 B1 | 6/2001 | Barry et al. |
| 7,129,391 B1 * | 10/2006 | Daniell ........................ 800/278 |
| 2007/0016985 A1 | 1/2007 | Miller et al. |

FOREIGN PATENT DOCUMENTS

| CN | 1687427 | * 10/2005 |
|---|---|---|
| EP | 0242246 | 10/1987 |
| EP | 0333033 | 9/1989 |
| WO | WO9302197 | 2/1993 |
| WO | WO9306487 | 4/1993 |
| WO | WO9319181 | 9/1993 |
| WO | WO9516776 | 6/1995 |
| WO | WO9518855 | 7/1995 |
| WO | WO9630517 | 10/1996 |
| WO | WO9630530 | 10/1996 |
| WO | 2005/012515 A2 | 2/2005 |
| WO | WO2005107437 | 11/2005 |
| WO | WO 2007/050715 | * 5/2007 |

OTHER PUBLICATIONS

Rosi et al. Science 312: 1027-1030 (May 2006).*
Torney, Francois, et al., Mesoporous Silica Nanoparticles Deliver DNA and Chemicals into Plants, Nature Nanotechnology, May 2007, pp. 295-300, vol. 2, Nature Publishing Group.
PCT International Search Report for International Application No. PCT/US2008/078860, Feb. 3, 2009, 4 pages.
PCT Written Opinion for International Application No. PCT/US2008/078860, dated Feb. 3, 2009.
International Preliminary Report on Patentability for International Application No. PCT/US2008/078860, dated Apr. 7, 2010.
Eggenerger et al., Direct Immunofluorescence of Plan Microtubules Based on Semiconductor Nanocrystals, Bioconjugate Chem. 2007, 18, pp. 1879-1886.

* cited by examiner

*Primary Examiner* — David T Fox
*Assistant Examiner* — Jared Shapiro
(74) *Attorney, Agent, or Firm* — Ronald S. Maciak; TraskBritt P.C.

(57) ABSTRACT

Provided are methods for introducing a molecule of interest into a plant cell comprising a cell wall. Methods are provided for genetically or otherwise modifying plants and for treating or preventing disease in plant cells comprising a cell wall.

25 Claims, 11 Drawing Sheets

US 8,722,410 B2

METHODS FOR TRANSFERRING MOLECULAR SUBSTANCES INTO PLANT CELLS

CROSS-REFERENCE TO RELATED APPLICATION

This application claims the benefit of U.S. Provisional Application No. 60/978,059, filed Oct. 5, 2007, the contents of which are incorporated by reference herein.

BACKGROUND OF THE INVENTION

Nanoparticles have unique properties that have been exploited for use in the delivery of DNA to cells. Among all nanoparticles investigated gold (Au) nanoparticles tend to be excellent candidates for delivery because of their low cytotoxicity and ease of functionalization with various ligands of biological significance. The commonly used synthesis of Au nanoparticles yields negatively charged (e.g., citrate coating) surface. Plasmid DNA, which may be sufficiently flexible to partially uncoil its bases, can be exposed to gold nanoparticles ("GNPs"). Under these partially uncoiled conditions, the negative charge on the DNA backbone may be sufficiently distant so that attractive van der Waals forces between the bases and the gold nanoparticle are sufficient to cause plasmid DNA to be attached to the surface of the gold particle.

In addition to metal nanoparticles, semi-conductor nanoparticles (e.g., quantum dots) ("QD") within the size range of 3-5 nm have also been used as carriers to deliver molecules into cells. DNA and proteins can be linked to the ligand attached to the QD surface (see, e.g., Patolsky, F., et al., J. Am. Chem. Soc. 125, 13918 (2003)). Carboxylic acid or amine coated QDs can be cross linked to molecules containing a thiol group see, e.g., Dubertret B, et. al., Science 298, 1759 (2002); Akerman, M. E., W. C. W. Chan, P. Laakkonen, S. N. Bhatia, E. Ruoslahti, Proc. Natl. Acad. Sci. U.S.A. 99, 12617 (2002); Mitchell, G. P., C. A. Mirkin, R. L. Letsinger, J. Am. Chem. Soc. 121, 8122 (1999)) or an N-hydroxysuccinimyl (NHS)ester group by using standard bioconjugation protocols (see, e.g., Pinaud, F., D. King, H.-P. Moore, S. Weiss, J. Am. Chem. Soc. 126, 6115 (2004); Bruchez, M., M. Moronne, P. Gin, S. Weiss, A. P. Alivisatos, Science 281, 2013 (1998)). An alternative way is conjugation of streptavidin coated QDs to biotinylated proteins, oligos or antibodies (see, e.g., Dahan M. et al., Science 302, 442 (2003); Pinaud, F., D. King, H.-P. Moore, S. Weiss, J. Am. Chem. Soc. 126, 6115 (2004); Dahan M. et al., Science 302, 442 (2003); Wu. X. Y., et al., Nature Biotechnol. 21, 41 (2003); Jaiswal, J. K., H. Mattoussi, J. M. Mauro, S. M. Simon, Nature Biotechnol. 21, 47 (2003); and Mansson, A., et al., Biochem. Biophys. Res. Commun. 314, 529 (2004).

Nanoparticles have been used to deliver plasmid DNA to a variety of animal cells. It has been found that when DNA coated nanoparticles are incubated with cells not having a cell wall, the cells take up the nanoparticles and begin expressing any genes encoded on the DNA. Where nanoparticle delivery to cells normally having a cell wall is desired, the cells wall is stripped before the addition of the particles to protoplasts of plant (see, Torney, F. et al., Nature Nanotechnol. 2, (2007). In plant cells, the cell wall stands as a barrier for the delivery of exogenously applied molecules. Many invasive methods, like gene gun (biolistics), microinjection, electroporation, and *Agrobacterium*, have been employed to achieve gene and small molecule delivery into these walled plant cells, but delivery of proteins have only been achieved by microinjection. Delivery of small molecules and proteins in the presence of a cell wall of a plant cell remains unexplored and would be advantageous in order to develop enabling technologies to be deployed in intact plant cell/tissue or organ for in vitro and in vivo manipulations The present invention relates to methods using nanoparticles to non-invasively deliver molecular substances into cells having a cell wall.

BRIEF SUMMARY OF THE INVENTION

The following embodiments are described in conjunction with systems, tools and methods which are meant to be exemplary and illustrative, and not limiting in scope.

According to the invention, there are provided methods of introducing a molecule of interest into a plant cell that includes a cell wall, the methods comprising: placing the plant cell having a cell wall in contact with a nanoparticle and a molecule of interest, and allowing uptake of the nanoparticle and the molecule of interest into the cell.

Further provided are methods of introducing a molecule of interest into a plant cell having a cell wall, the methods comprising: placing the plant cell having a cell wall in contact with a nanoparticle and a molecule capable of treating the disease and allowing uptake of the nanoparticle and the molecule capable of treating the disease into the cell.

In addition to the exemplary aspects and embodiments described above, further aspects and embodiments will become apparent in view of the following descriptions.

BRIEF DESCRIPTION OF THE DRAWINGS

FIG. 2, Panel B, shows similar NT1 cells viewed under a fluorescent microscope with active chloroplasts autofluorescing in red.

FIG. 3, Panel A, shows a DIC image of cells treated with SAMSA fluorescein alone while FIG. 3, Panel B, shows the fluorescent image of the same cells. FIG. 3, Panel C, shows a DIC image of cells treated with SAMSA fluorescein coated GNPs while FIG. 3, Panel D, shows the fluorescent image of the SAMSA fluorescein coated GNPs-treated cells. Positions of Nucleus (Nu) and Cell Wall (CW) are as indicated.

DETAILED DESCRIPTION OF THE INVENTION

Figure 1:
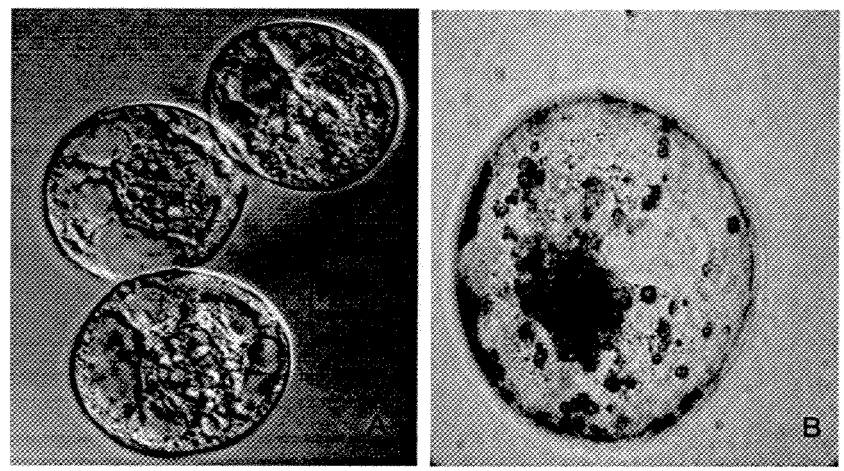
FIG. 1 depicts photographs of single cells of BY2 viewed using a differential Interference Contrast microscope attached to a confocal imaging system (Panel A). Panel B shows a light microscopic view of a single cell from a BY2 variant that is stained with I2KI to highlight the plastid (Amyloplast).

In the description and tables which follow, a number of terms are used. In order to provide a clear and consistent understanding of the specification and claims, including the scope to be given such terms, the following definitions are provided:

Backcrossing. Backcrossing may be a process in which a breeder repeatedly crosses hybrid progeny back to one of the parents, for example, a first generation hybrid $F_1$ with one of the parental genotypes of the $F_1$ hybrid.

Embryo. The embryo may be the small plant contained within a mature seed.

Nanoparticle. A microscopic particle with at least one nanoscale dimension, usually less than 100 nm. Nanoparticles suitable for use in the present invention may have a size of 1 nm-0.4 um. A quantum dot may have a median diameter of 1 nm-10 nm, preferably 2-4 nm. The nanoparticle may be selected from: gold nanoparticles, gold coated nanoparticles, porous nanoparticles, mesoporous nanoparticles, silica nanoparticles, polymer nanoparticles, tungsten nanoparticles, gelatin nanoparticles, nanoshells, nanocores, nanospheres, nanorods, magnetic nanoparticles, and combinations thereof.

Quantum dot. A quantum dot is a semiconductor nanostructure that confines the motion of conduction band electrons, valence band holes, or excitons (bound pairs of conduction band electrons and valence band holes) in all three spatial directions. The confinement can be due to electrostatic potentials (generated by external electrodes, doping, strain, impurities), the presence of an interface between different semiconductor materials (e.g. in core-shell nanocrystal systems), the presence of the semiconductor surface (e.g. semiconductor nanocrystal), or a combination of these. A quantum dot can have a discrete quantized energy spectrum. The corresponding wave functions are spatially localized within the quantum dot, but extend over many periods of the crystal lattice. A quantum dot contains a small finite number (of the order of 1-100) of conduction band electrons, valence band holes, or excitons (i.e., a finite number of elementary electric charges).

Resistant to Glyphosate. Resistance to a dosage of glyphosate refers to the ability of a plant to survive (i.e. the plant may be not killed) by that dosage of glyphosate. In some cases, tolerant plants may temporarily yellow or otherwise exhibit some glyphosate-induced injury (e.g., excessive tillering and/or growth inhibition), but recover.

Stabilized. Stabilized refers to characteristics of a plant that are reproducibly passed from one generation to the next generation of inbred plants of the same variety.

Uptake. Uptake refers to the translocation of a particle, such as a nanoparticle, for example gold or quantum dots, across a cell wall or a cellular membrane, wherein the translocation does not occur solely as a result of momentum imparted to the particle by something other than the cell into which the particle is being uptaken. Non-limiting examples of devices or methods which cause translocation of a particle across a cell wall or a cell membrane solely as a result of momentum imparted to the particle are biolistic, gene gun, microinjection, and/or impalefection technologies.

According to embodiments the invention, there may be provided a method of introducing a molecule of interest into a plant cell comprising a cell wall, the method comprising placing a nanoparticle containing, and a molecule of interest in contact with, the plant cell and allowing uptake of the nanoparticle across the plant cell wall. In particular aspects of invention, the nanoparticle may be any nanoparticle and may reversibly or irreversibly contain, be coated with, or otherwise be bound to and/or carry a molecule of interest. In certain embodiments, a molecule of interest may be introduced to the nanoparticles before contact with a plant cell having a cell wall or concurrently with the introduction of the nanoparticle to a plant cell having a cell wall. Examples of nanoparticles that can be used in embodiments of the present invention include, but are not limited to, gold, quantum dots, gold coated nanoparticles, porous nanoparticles, mesoporous nanoparticles, silica nanoparticles, polymer nanoparticles, tungsten nanoparticles, gelatin nanoparticles, nanoshells, nanocores, nanospheres, nanorods, magnetic nanoparticles, and/or combinations thereof.

According to embodiments of the present invention, a plant cell having a cell wall may be any plant cell comprising an intact and whole cell wall. Examples of cells having a cell wall include, but are not limited to, algal, tobacco, carrot, maize, canola, rapeseed, cotton, palm, peanut, soybean, sugarcane, *Oryza* sp., *Arabidopsis* sp., and *Ricinus* sp., preferably tobacco, carrots maize, cotton, canola, soybean and sugarcane; more preferably tobacco and carrots. Embodiments of the invention may include cells comprising a cell wall from any tissue or wherever they are found, including but not limited to, in embryos, meristematic cells, callus, pollen, leaves, anthers, roots, root tips, flowers, seeds, pods, stems, and tissue culture.

In embodiments of the invention, a molecule of interest may be any molecule that can be delivered to a plant cell according to the present invention. Molecules of interest, or components of molecules of interest, may comprise, but are not limited to, nucleic acids, DNA, RNA, RNAi molecules, genes, plasmids, cosmids, YACs, BACs, polypeptides, enzymes, hormones, glyco-peptides, sugars, fats, signaling peptides, antibodies, vitamins, messengers, second messengers, amino acids, cAMP, drugs, herbicides, fungicides, antibiotics, and/or combinations thereof.

Embodiments of the invention include methods for the prevention or treatment of disease. Non-limiting example embodiments include the delivery of fungicides, antibiotics, and/or other drugs to cells in need thereof using methods of the present invention.

In particular embodiments of the invention, the surface of the nanoparticle may be functionalized, which may, for example, allow for targeted uptake or allow for reversible or irreversible binding of other substances to the surface of the nanoparticle. By way of non-limiting example, the surface of a nanoparticle (e.g., gold nanoparticle or quantum dots) might be functionalized with a self-assembled monolayer of, for example, alkanethiolates, which can be further functionalized or derivatized. In a further non-limiting example, the surface of a nanoparticle may be derivatized with linkers which themselves may be further functionalized or derivatized. In one embodiment, a nanoparticle may be PEGylated. In other embodiments, the nanoparticle may comprise, or may be multifunctionalized with, one or more of a core (active or inactive), a steric coat (active or inert), a cleavable linkage, and/or a targeting molecule or ligand.

In aspects of the invention, the nanoparticle may be uptaken into various parts of cells. Examples of locations that a nanoparticle may be uptaken into include, but are not limited to, cytosol, nucleus, tonoplasts, plastids, etioplasts, chromoplasts, leucoplasts, elaioplasts, proteinoplasts, amyloplasts, chloroplasts, and the lumen of a double membrane. In other embodiments of the invention, nanoparticle uptake into a cell comprising a cell wall may occur via the symplastic or apoplastic pathway.

Additional embodiments of the invention include genetically modified plant cells and methods for generating them, wherein the plant cells have one or more nucleic acids introduced therein via methods of the present invention. In one example of an embodiment, a plasmid comprising a gene of interest and a selectable marker may be in introduced into a plant cell having a cell well via a nanoparticle according to the present invention. In further embodiments, stable transformants may be selected that have stably integrated the gene of interest and/or the selectable marker. In alternative embodiments, a plant cell now comprising the gene of interest may be propagated to produce other cells comprising a molecule of interest. In other embodiments, plant cells now comprising a molecule of interest may be a regenerable cell that may be used to regenerate a whole plant including the molecule of interest.

In another aspect, the present invention provides methods of creating regenerable plant cells comprising a molecule of interest for use in tissue culture. The tissue culture will preferably be capable of regenerating plants having substantially the same genotype as the regenerable cells. The regenerable cells in such tissue cultures can be embryos, protoplasts, meristematic cells, callus, pollen, leaves, anthers, roots, root tips, flowers, seeds, pods or stems. Still further, an embodiment of the invention provides plants regenerated from the tissue cultures of the invention.

Alternatively, the present invention provides a method of introducing a desired trait into a plant cell having a cell wall, wherein the method comprises: placing a nanoparticle and a molecule of interest capable of providing the desired trait to the plant cell in contact with the cell and allowing uptake of the nanoparticle across the cell wall. Examples of desired traits include, but are not limited to, traits selected from male sterility, herbicide resistance, insect resistance, and resistance to bacterial disease, fungal disease, and/or viral disease.

Further aspects of the invention provide for the methods of generating of stabilized plant lines comprising a desired trait or molecule of interest, wherein the desired trait or molecule of interest may be first introduced by uptake of a nanoparticle across a plant cell wall. Methods of generating stabilized plant lines are well known to one of ordinary skill in the art and may include techniques such as, but not limited to, selfing, backcrosses, hybrid production, crosses to populations, and the like. All plants and plant cells comprising a desired trait or molecule of interest first introduced into the plant cell (or its predecessors) by uptake of a nanoparticle across a cell wall are within the scope of this invention. Advantageously, the plant cells comprising a desired trait or molecule of interest first introduced into the plant or cell (or its predecessors) by uptake of a nanoparticle across a cell wall can be used in crosses with other, different, plant cells to produce first generation ($F_1$) hybrid cells, seeds, and/or plants with superior characteristics.

In embodiments wherein the molecule of interest comprises one or more gene(s), the gene(s) may be a dominant or recessive allele. By way of example, the gene(s) will confer such traits as herbicide resistance, insect resistance, resistance for bacterial resistance, fungal resistance, viral disease resistance, male fertility, male sterility, enhanced nutritional quality, and industrial usage.

With the advent of molecular biological techniques that have allowed the isolation and characterization of genes that encode specific protein or RNA products (e.g. RNAi), scientists in the field of plant biology developed a strong interest in engineering the genome of cells to contain and express foreign genes, or additional or modified versions of native or endogenous genes (perhaps driven by different promoters) in order to alter the traits of a cell in a specific manner. Such foreign additional and/or modified genes are referred to herein collectively as "transgenes." Over the last fifteen to twenty years, several methods for producing transgenic cells have been developed and, in particular embodiments, the present invention relates to transformed versions of cells and methods of producing them via introducing into a cell having a cell wall a transgene via uptake of a nanoparticle across a cell wall. In embodiments of the invention, the transgene may be contained in an expression vector.

Cell transformation may involve the construction of an expression vector which will function in a particular cell. Such a vector may comprise DNA that includes a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed cells using transformation methods as described herein to incorporate transgene(s) into the genetic material of a plant cell comprising a cell wall.

Expression Vectors for Uptake via Nanoparticle: Marker Genes

Expression vectors may include at least one genetic marker, operably linked to a regulatory element (a promoter, for example) that allows transformed cells containing the marker to be either recovered by negative selection (i.e., inhibiting growth of cells that do not contain the selectable marker gene) or by positive selection (i.e., screening for the product encoded by the genetic marker). Many selectable marker genes for transformation are well known in the transformation arts and include, for example, genes that code for enzymes that metabolically detoxify a selective chemical agent which may be an antibiotic or an herbicide, or genes that encode an altered target which may be insensitive to the inhibitor. A few positive selection methods are also known in the art.

One commonly used selectable marker gene suitable for plant transformation may include the neomycin phosphotransferase II (nptII) gene under the control of plant regulatory signals, which confers resistance to kanamycin. See, e.g., Fraley et al., Proc. Natl. Acad. Sci. U.S.A., 80: 4803 (1983). Another commonly used selectable marker gene may be the hygromycin phosphotransferase gene, which confers resistance to the antibiotic hygromycin. See, e.g., Vanden Elzen et al., Plant Mol. Biol., 5: 299 (1985).

Additional selectable marker genes of bacterial origin that confer resistance to antibiotics include gentamycin acetyl transferase, streptomycin phosphotransferase, aminoglycoside-3'-adenyl transferase, and the bleomycin resistance determinant. See Hayford et al., Plant Physiol. 86: 1216 (1988), Jones et al., Mol. Gen. Genet., 210: 86 (1987), Svab et al., Plant Mol. Biol. 14: 197 (1990), Hille et al., Plant Mol. Biol. 7: 171 (1986). Other selectable marker genes confer resistance to herbicides such as glyphosate, glufosinate or bromoxynil. See Comai et al., Nature 317: 741-744 (1985), Gordon-Kamm et al., Plant Cell 2: 603-618 (1990) and Stalker et al., Science 242: 419-423 (1988).

Other selectable marker genes suitable for plant transformation are not of bacterial origin. These genes include, for example, mouse dihydrofolate reductase, plant 5-enolpyruvylshikimate-3-phosphate synthase and plant acetolactate synthase. See Eichholtz et al., Somatic Cell Mol. Genet. 13: 67 (1987), Shah et al., Science 233: 478 (1986), Charest et al., Plant Cell Rep. 8: 643 (1990).

Another class of marker genes suitable for plant transformation requires screening of presumptively transformed plant cells rather than direct genetic selection of transformed cells for resistance to a toxic substance, such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening transformed cells include β-glucuronidase (GUS), β-galactosidase, luciferase and chloramphenicol acetyltransferase. See Jefferson, R. A., Plant Mol. Biol. Rep. 5: 387 (1987), Teeri et al., EMBO J. 8: 343 (1989), Koncz et al., Proc. Natl. Acad. Sci. U.S.A. 84: 131 (1987), DeBlock et al., EMBO J. 3: 1681 (1984).

Recently, in vivo methods for visualizing GUS activity that do not require destruction of plant tissue have been made available. Molecular Probes publication 2908, Imagene Green. T M., p. 1-4 (1993) and Naleway et al., J. Cell Biol. 115: 151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, genes encoding Fluorescent Proteins (e.g. GFP, EGFP, EBFP, ECFP, and YFP) have been utilized as markers for gene expression in prokaryotic and eukaryotic cells. See Chalfie et al., Science 263: 802 (1994). Fluorescent proteins and mutations of fluorescent proteins may be used as screenable markers.

Expression Vectors for Uptake via Nanoparticle: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA that may be upstream from the start of transcription and that may be involved in recognition and binding of RNA polymerase and other proteins to initiate transcription. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type" specific promoter primarily drives expression in certain cell types in one or more organs, for example, vascular cells in roots or leaves. An "inducible" promoter may be a promoter which may be under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter may be a promoter which may be active under most environmental conditions.

A. Inducible Promoters

An inducible promoter may be operably linked to a gene for expression in a cell. Optionally, the inducible promoter may be operably linked to a nucleotide sequence encoding a signal sequence which may be operably linked to a gene for expression in a cell. With an inducible promoter, the rate of transcription increases in response to an inducing agent.

Any inducible promoter can be used in the instant invention. See Ward et al., Plant Mol. Biol. 22: 361-366 (1993). Exemplary inducible promoters include, but are not limited to: those from the ACEI system that responds to copper (Mett et al., PNAS 90: 4567-4571 (1993)); In2 gene from maize that responds to benzenesulfonamide herbicide safeners (Hershey et al., Mol. Gen. Genetics 227: 229-237 (1991) and Gatz et al., Mol. Gen. Genetics 243: 32-38 (1994)); and Tet repressor from Tn10 (Gatz et al., Mol. Gen. Genetics 227: 229-237 (1991)). A particularly useful inducible promoter may be a promoter that responds to an inducing agent to which plants do not normally respond. An exemplary inducible promoter may be the inducible promoter from a steroid hormone gene, the transcriptional activity of which may be induced by a glucocorticosteroid hormone. Schena et al., Proc. Natl. Acad. Sci. U.S.A. 88: 0421 (1991).

B. Constitutive Promoters

A constitutive promoter may be operably linked to a gene for expression in a cell or the constitutive promoter may be operably linked to a nucleotide sequence encoding a signal sequence which may be operably linked to a gene for expression in a cell.

Different constitutive promoters can be utilized in the instant invention. Exemplary constitutive promoters include, but are not limited to: promoters from plant viruses, such as the 35S promoter from CaMV (Odell et al., Nature 313: 810-812 (1985)); promoters from rice actin genes (McElroy et al., Plant Cell 2: 163-171 (1990)); ubiquitin (Christensen et al., Plant Mol. Biol. 12: 619-632 (1989) and Christensen et al., Plant Mol. Biol. 18: 675-689 (1992)); pEMU (Last et al., Theor. Appl. Genet. 81: 581-588 (1991)); MAS (Velten et al., EMBO J. 3: 2723-2730 (1984)); and maize H3 histone (Lepetit et al., Mol. Gen. Genetics 231: 276-285 (1992) and Atanassova et al., Plant Journal 2 (3): 291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-Specific or Tissue-Preferred Promoters

A tissue-specific promoter may be operably linked to a gene for expression in a cell. Optionally, the tissue-specific promoter may be operably linked to a nucleotide sequence encoding a signal sequence which may be operably linked to a gene for expression in a cell. Plants transformed with a gene of interest operably linked to a tissue-specific promoter can produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., Science 23: 476-482 (1983) and Sengupta-Gopalan et al., Proc. Natl. Acad. Sci. U.S.A. 82: 3320-3324 (1985)); a leaf-specific and light-induced promoter such as that from cab or rubisco (Simpson et al., EMBO J. 4(11): 2723-2729 (1985) and Timko et al., Nature 318: 579-582 (1985)); an anther-specific promoter such as that from LAT52 (Twell et al., Mol. Gen. Genetics 217: 240-245 (1989)); a pollen-specific promoter such as that from Zm13 (Guerrero et al., Mol. Gen. Genetics 244: 161-168 (1993)) or a microspore-preferred promoter such as that from apg (Twell et al., Sex. Plant Reprod. 6: 217-224 (1993)).

Transport of protein produced by transgenes to a subcellular compartment, such as the chloroplast, vacuole, peroxisome, glyoxysome, cell wall or mitochondrion or for secretion into the apoplast, can be accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein may be ultimately compartmentalized. Alternatively such subcellular compartment targeting proteins can be directly linked to a nanoparticle to direct the nanoparticle coated with the molecule of interest to the desired subcellular compartment.

The presence of a signal sequence directs a polypeptide to either an intracellular organelle or subcellular compartment, or for secretion to the apoplast. Many signal sequences are known in the art. See, e.g., Becker et al., Plant Mol. Biol. 20: 49 (1992), Close, P. S., Master's Thesis, Iowa State University (1993), Knox, C., et al., "Structure and Organization of Two Divergent Alpha-Amylase Genes from Barley", Plant Mol. Biol. 9: 3-17 (1987), Lerner et al., Plant Physiol. 91: 124-129 (1989), Fontes et al., Plant Cell 3: 483-496 (1991), Matsuoka et al., Proc. Natl. Acad. Sci. 88: 834 (1991), Gould et al., J. Cell. Biol. 108: 1657 (1989), Creissen et al., Plant J. 2: 129 (1991), Kalderon, et al., A short amino acid sequence able to specify nuclear location, Cell 39: 499-509 (1984), Steifel, et al., Expression of a maize cell wall hydroxyproline-rich glycoprotein gene in early leaf and root vascular differentiation, Plant Cell 2: 785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114: 92-6 (1981).

In aspects of the invention, the transgenic plant provided for commercial production of foreign protein may be a cell or a plant. In other aspects, the biomass of interest may be seed. For the relatively small number of transgenic plants that show higher levels of expression, a genetic map can be generated primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269: 284 (1993). Map information concerning chromosomal location may be useful for proprietary protection of a subject transgenic plant. If unauthorized propagation may be undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques.

Likewise, agronomic genes can be expressed in transformed cells or their progeny. More particularly, plants can be genetically engineered via the methods of the invention to express various phenotypes of agronomic interest. Exemplary genes that may be used in this regard include, but are not limited to, those categorized below.

1. Genes that Confer Resistance to Pests or Disease and that Encode:

A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, e.g., Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (Arabidops may be RSP2 gene for resistance to *Pseudomonas syringae*).

B) A gene conferring resistance to a pest, such as soybean cyst nematode. See e.g., PCT Application WO 96/30517; PCT Application WO 93/19181.

C) A *Bacillus thuringiensis* protein, a derivative thereof or a synthetic polypeptide modeled thereon. See, e.g., Geiser et al., Gene 48: 109 (1986), which discloses the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D) A lectin. See, for example, the disclosure by Van Damme et al., Plant Molec. Biol. 24: 25 (1994), who disclose the nucleotide sequences of several *Clivia miniata* mannose-binding lectin genes.

E) A vitamin-binding protein, such as avidin. See PCT application US93/06487. The application teaches the use of avidin and avidin homologues as larvicides against insect pests.

F) An enzyme inhibitor, for example, a protease or proteinase inhibitor or an amylase inhibitor. See, e.g., Abe et al., J. Biol. Chem. 262: 16793 (1987) (nucleotide sequence of rice cysteine proteinase inhibitor), Huub et al., Plant Molec. Biol. 21: 985 (1993) (nucleotide sequence of cDNA encoding tobacco proteinase inhibitor I), Sumitani et al., Biosci. Biotech. Biochem. 57: 1243 (1993) (nucleotide sequence of *Streptomyces nitrosporeus* .alpha.-amylase inhibitor) and U.S. Pat. No. 5,494,813 (Hepher and Atkinson, issued Feb. 27, 1996).

G) An insect-specific hormone or pheromone such as an ecdysteroid or juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

H) An insect-specific peptide or neuropeptide which, upon expression, disrupts the physiology of the affected pest. For example, see the disclosures of Regan, J. Biol. Chem. 269: 9 (1994) (expression cloning yields DNA coding for insect diuretic hormone receptor), and Pratt et al., Biochem. Biophys. Res. Comm. 163: 1243 (1989) (an allostatin may be identified in *Diploptera puntata*). See also U.S. Pat. No. 5,266,317 to Tomalski et al., which discloses genes encoding insect-specific, paralytic neurotoxins.

I) An insect-specific venom produced in nature by a snake, a wasp, or any other organism. For example, see Pang et al., Gene 116: 165 (1992), for disclosure of heterologous expression in plants of a gene coding for a scorpion insectotoxic peptide.

J) An enzyme responsible for a hyperaccumulation of a monoterpene, a sesquiterpene, a steroid, hydroxamic acid, a phenylpropanoid derivative or another non-protein molecule with insecticidal activity.

K) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hornworm chitinase, and Kawalleck et al., Plant Molec. Biol. 21: 673 (1993), who provide the nucleotide sequence of the parsley ubi4-2 polyubiquitin gene.

L) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a maize calmodulin cDNA clone.

M) A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N) A membrane permease, a channel former or a channel blocker. For example, see the disclosure of Jaynes et al., Plant Sci 89: 43 (1993), of heterologous expression of a cecropin-β lytic peptide analog to render transgenic tobacco plants resistant to *Pseudomonas solanacearum*.

O) A viral-invasive protein or a complex toxin derived therefrom. For example, the accumulation of viral coat proteins in transformed plant cells imparts resistance to viral infection and/or disease development effected by the virus from which the coat protein gene may be derived, as well as by related viruses. See Beachy et al., Ann. rev. Phytopathol. 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P) An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q) A virus-specific antibody. See, for example, Tavladoraki et al., Nature 366: 469 (1993), who show that transgenic plants expressing recombinant antibody genes are protected from virus attack.

R) A developmental-arrestive protein produced in nature by a pathogen or a parasite. For example, fungal endo α-1,4-D-polygalacturonases facilitate fungal colonization and plant nutrient release by solubilizing plant cell wall homo-α-1,4-D-galacturonase. See Lamb et al., Bio/Technology 10: 1436 (1992). The cloning and characterization of a gene which encodes a bean endopolygalacturonase-inhibiting protein may be described by Toubart et al., Plant J. 2: 367 (1992).

S) A developmental-arrestive protein produced in nature by a plant. For example, Logemann et al., Bio/Technology 10: 305 (1992), have shown that transgenic plants expressing the barley ribosome-inactivating gene have an increased resistance to fungal disease.

2. Genes that Confer Resistance to an Herbicide:

A) An herbicide that inhibits the growing point or meristem, such as an imidazolinone or a sulfonylurea. Exemplary genes in this category code for mutant ALS and AHAS enzyme as described, for example, by Lee et al., EMBO J. 7: 1241 (1988), and Miki et al., Theor. Appl. Genet. 80: 449 (1990), respectively.

B) Glyphosate (resistance conferred by, e.g., mutant 5-enolpyruvylshikimate-3-phosphate synthase (EPSPS) genes (via the introduction of recombinant nucleic acids and/or various forms of in vivo mutagenesis of native EPSPs genes), aroA genes and glyphosate acetyl transferase (GAT) genes, respectively), other phosphono compounds such as glufosinate (phosphinothricin acetyl transferase (PAT) genes from *Streptomyces* species, including *Streptomyces hygroscopicus* and *Streptomyces viridichromogenes*), and pyridinoxy or phenoxy proprionic acids and cyclohexones (AC-Case inhibitor-encoding genes), See, for example, U.S. Pat. No. 4,940,835 to Shah, et al. and U.S. Pat. No. 6,248,876 to Barry et. al., which disclose nucleotide sequences of forms of EPSPs which can confer glyphosate resistance to a plant. A DNA molecule encoding a mutant aroA gene can be obtained under ATCC accession number 39256, and the nucleotide sequence of the mutant gene may be disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene may be provided in European application No. 0 242 246 to Leemans et al., DeGreef et al., Bio/Technology 7: 61 (1989), describe the production of transgenic plants that express chimeric bar genes coding for PAT activity. Exemplary of genes conferring resistance to phenoxy proprionic acids and cyclohexones, such as sethoxydim and haloxyfop include the Acc1-S1, Acc1-S2 and Acc1-S3 genes described by Marshall et al., Theor. Appl. Genet. 83: 435 (1992). GAT genes capable of conferring glyphosate resistance are described in WO 2005012515 to Castle et. al. Genes conferring resistance to 2,4-D, fop and pyridyloxy auxin herbicides are described in WO 2005107437 assigned to Dow AgroSciences LLC.

C) An herbicide that inhibits photosynthesis, such as a triazine (psbA and gs+ genes) or a benzonitrile (nitrilase gene). Przibila et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase may be described by Hayes et al., Biochem. J. 285: 173 (1992).

3. Genes that Confer or Contribute to a Value-Added Trait, Such as:

A) Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89: 2624 (1992).

B) Decreased phytate content—1) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an *Aspergillus niger* phytase gene. 2) A gene could be introduced that reduced phytate content. In maize for example, this could be accomplished by cloning and then reintroducing DNA associated with the single allele which may be responsible for maize mutants characterized by low levels of phytic acid. See Raboy et al., Maydica 35: 383 (1990).

C) Modified carbohydrate composition effected, for example, by transforming plants with a gene coding for an enzyme that alters the branching pattern of starch. See Shiroza et al., J. Bacteol. 170: 810 (1988) (nucleotide sequence of *Streptococcus* mutants fructosyltransferase gene), Steinmetz et al., Mol. Gen. Genet. 20: 220 (1985) (nucleotide sequence of *Bacillus subtil* may be levansucrase gene), Pen et al., Bio/Technology 10: 292 (1992) (production of transgenic plants that express *Bacillus lichenifonnmay* be α-amylase), Elliot et al., Plant Molec. Biol. 21: 515 (1993) (nucleotide sequences of tomato invertase genes), Sogaard et al., J. Biol. Chem. 268: 22480 (1993) (site-directed mutagenesmay be of barley α-amylase gene), and Fisher et al., Plant Physiol. 102: 1045 (1993) (maize endosperm starch branching enzyme II).

EXAMPLES

The present invention is further described in the following examples, which are offered by way of illustration and are not intended to limit the invention in any manner.

Example 1

Preparation of Single Cell Plant Material

Figure 2:
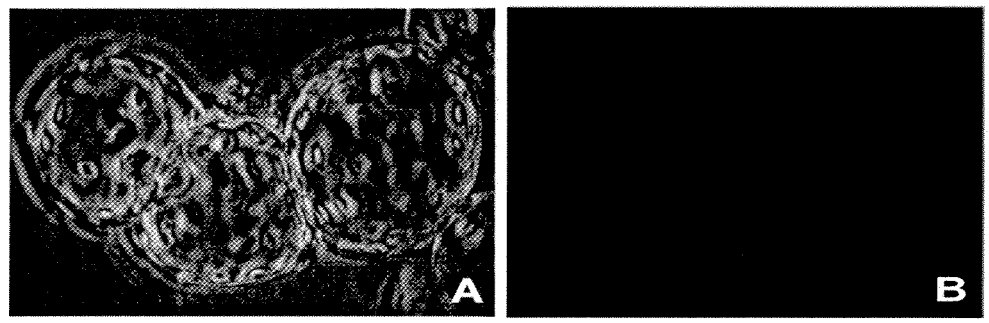
FIG. 2, Pane A depicts photoautotrophic cells of tobacco (NT1) maintained in minimal medium and 5% carbon dioxide as seen in a light microscope, where prominent chloroplasts are visible.

Both BY2 cells and NT1 cells were used. BY2 cells are a non-green, fast growing tobacco cell line. NT1 cells are photoautotrophic cells isolated from tobacco. Three to four days prior to transformation, a one-week-old suspension culture was subcultured to fresh medium by transfer of 2 ml of NT1 or BY2 culture into 40 ml NT1B or LSBY2 media containing 50 nM DAS-PMTI-1 (a microtubule inhibitor) and 0.5-0.1% (v/v) DMSO in a 250-mL flask. Single cells were collected either at four days or seven days after the microtubule inhibitor treatment. The BY2 single cells used were processed through a Beckman Flow cytometer to count the viable cells. There were 658250 viable cells/ml with a mean diameter of 10.43 um and a volume of 593.8 $\mu m^3$. As visible in FIG. 1, all the cells were single cells (the pair in FIG. 1 has overlapping edges). The cells were examined using a Differential Interference Contrast (DIC) microscope attached to a confocal imaging system (Panel A). Panel B shows a light microscopic view of single cell from BY2 cells (EP12% medium habituated and maintained cultures) that were stained with I2KI to highlight the plastid (Amyloplast). As is visible therein, single cells of BY2 cells comprise large numbers of plastids (amyloplasts) distributed throughout the cytoplasm of the cell. FIG. 2, Panel A, depicts light microscope photoautotrophic cells of tobacco (NT1) having prominent chloroplasts, which were maintained in minimal medium and 5% carbon dioxide. These cells were sub cultured once in every 14 days by transferring 1 ml of suspension at $3.0OD^{600}$. FIG. 2, Panel B, shows similar NT1 cells as viewed under a fluorescent microscope in which the active chloroplasts can bee seen to be autofluorescing in red.

The cell types described above were used as target cells for transformation. The green cells (NT1 cells) are a optimum cell type to track a nanoparticle into the chloroplast as they have few cells in a given cluster and are hyaline. In addition, the cells have very prominent chloroplasts that autofluoresce red (as visible in FIG. 2, Panel B).

Example 2

Nanoparticle Preparation and Treatment of Cells

To determine if cells took up fluorescent dye in culture, single cells and multicellular standard aggregate suspension culture of BY2 cells was used. The cell suspension cultures were exposed to SAMSA fluorescein (5-((2-(and-3)-S-(acetylmercapto) succinoyl)amino) fluorescein) from Molecular Probes in the absence of nanoparticles for 20 minutes and then were briefly washed before being observed under a fluorescent microscope.

Gold nanoparticles (GNP) were coated with SAMSA fluorescein as per the product technical guidelines (available on the world wide web at probes.invitrogen.com/media/pis/mp00685.pdf). Gold-fluorescein conjugate was prepared by using a method described hereafter. 1 mg of SAMSA fluorescein was dissolved in 100 μl of 0.1 M NaOH and vortexed for 15 minutes to remove the acetyl group protecting the thiol. This activated SAMSA was then mixed with 100 μl of 150 nm gold colloids (~109 particles/ml). The resulting solution was then incubated for 1 hour to ensure the completion of the reaction. Then 50 μL of 1M HCl was added to neutralize the solution. It was centrifuged at 3000 RPM for 30 minutes and supernatant was removed. The yellow pellet obtained was re-suspended in 200 μL of 0.1 M PBS, resulting in an orange colored solution. This purification step was repeated 2 times to ensure removal of free SAMSA fluorescein. The mode of attachment of SAMSA to gold is mainly via thiol bonding. Due to the significant electrostatic repulsion (SAMSA is dianionic at pH>7), SAMSA is thought to lie perpendicular to the gold colloidal surface. The particles showed clear fluorescence without any background when observed under a DIC and multiphoton confocal microscope. 20 and 40 μl of coated gold nanoparticle were transferred to 500 μl of BY2/

NT1 tobacco suspensions or Photoautotrophic tobacco cells and incubated for 20 minutes in dark.

After incubation, 50 μl aliquots of cell suspensions were mounted on microscopic perfusion slides and observed under the microscope to track the particles. In addition, aliquots of samples were prepared for microscopic observation at 2-20 hrs after the 20 minute incubation.

Example 3

Figure 3:
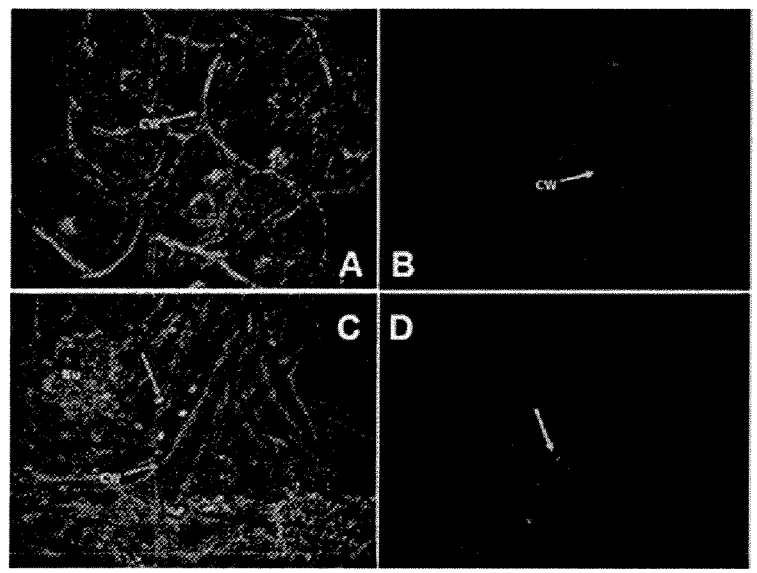
FIG. 3 shows BY2 suspension aggregates treated with SAMSA fluorescein alone and with SAMSA fluorescein coated GNPs.

Fluorescein Coated Nanoparticle Delivery and Accumulation in BY2/NT1 Cell Aggregates and in Nucleus and Plastids of Single Photoautotrophic Tobacco Cells The BY2/NT1 suspension aggregates treated with SAMSA fluorescein alone and with SAMSA fluorescein coated GNPs were examined under low and high magnification using DIC, bright-field, and fluorescent scopes. FIG. 3, Panel A, shows a DIC image of cells treated with SAMSA fluorescein alone, while FIG. 3, Panel B, shows a fluorescent image of the same cells. FIG. 3, Panel C, shows a DIC image of cells treated with SAMSA fluorescein coated GNPs, while FIG. 3, Panel D, shows the fluorescent image of the SAMSA fluorescein coated GNPs-treated cells. As is clearly visible in FIG. 3, Panel B, only the cell walls of the cells treated with SAMSA fluorescein alone stained with the fluorescein and very little other background fluorescence was visible. This indicates that the cells did not uptake the SAMSA fluorescein in the absence of nanoparticles.

Figure 4:
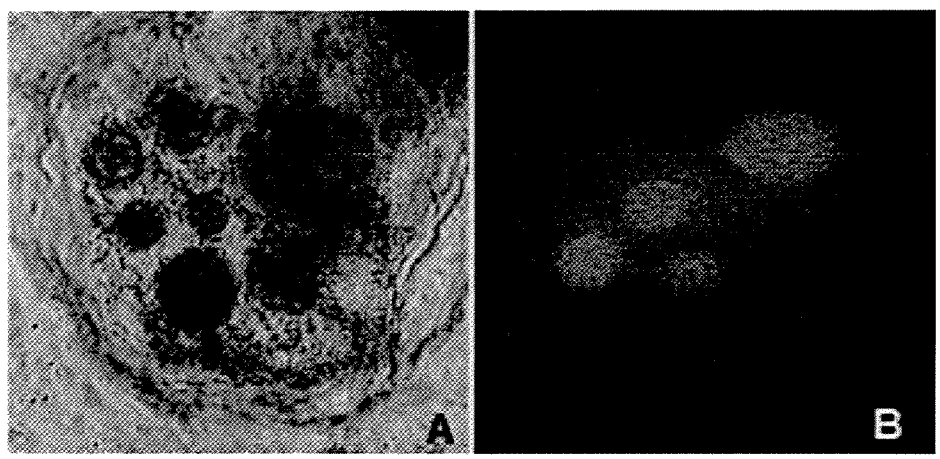
FIG. 4 shows SAMSA fluorescein coated GNP-treated single cells under high magnification. Panel B shows the presence of large number of GNPs in the nucleolus. Panel A shows a bright-field view of the same nucleolus shown in Panel B under a different plane of focus.

In contrast, the SAMSA fluorescein-coated GNPs were tracked into the cells and the nucleus (Nu), as seen in FIG. 3, Panel D. It was clear from the DIC observations that the SAMSA fluorescein-coated GNPs were found in all compartments of the cells, except vacuoles. The cytoplasmic strands lining the vacuoles also had SAMSA fluorescein-coated GNPs in addition to the nuclear compartment. The nanoparticles do not appear to have been hindered in their transport across the cell walls. Thus, the accumulation of SAMSA fluorescein coated GNPs seems to be in the symplastic, as opposed to the apoplastic, continuum. Further examination of the SAMSA fluorescein-coated GNP treated single cells under high magnifications showed the presence of a large number of GNPs in nucleolus and it appeared that the GNPs are preferentially accumulated in these organelles (FIG. 4: Panel B). Panel A of FIG. 4 shows a bright-field image of the same nucleus as Panel B under a different plane of focus.

Figure 5:
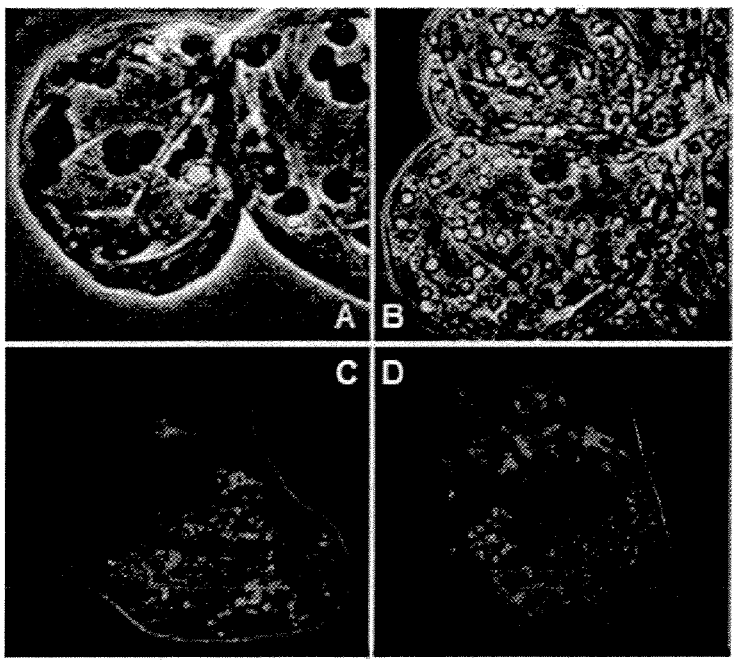
FIG. 5 shows photoautotrophic cells treated with SAMSA fluorescein coated GNP. Panel A shows hyaline cells in 3-4 cell clusters with large chloroplasts lining the inner side of the cell wall. Panel B shows accumulation of nanoparticles in the chloroplast. Panels C and D show higher power magnification of a single chloroplast using a fluorescent microscope. Nanoparticles are visible in the membrane lamellations of the chloroplast and interspersed among the red autofluorescing chlorophyll pigments.

FIG. 5. shows photoautotrophic cells treated with SAMSA fluorescein coated GNP. Panel A shows very hyaline cells in 3-4 cell clusters with large chloroplasts lining the inner side of the cell wall. Panel B shows accumulation of nanoparticles in the chloroplast. Panels C and D show higher power magnification of a single chloroplast using a fluorescent microscope. Nanoparticles are visible in the membrane lamellations of the chloroplast and interspersed among the red autofluorescing chlorophyll pigments.

Thus, the live photoautotrophic cell tracking with the bright-field and fluorescent microscopes in the real time demonstrated that the nanoparticles were accumulating in both membrane and chloroplast matrix. The particles could be also tracked in the lumen of the double membrane of the chloroplast.

Figure 6:
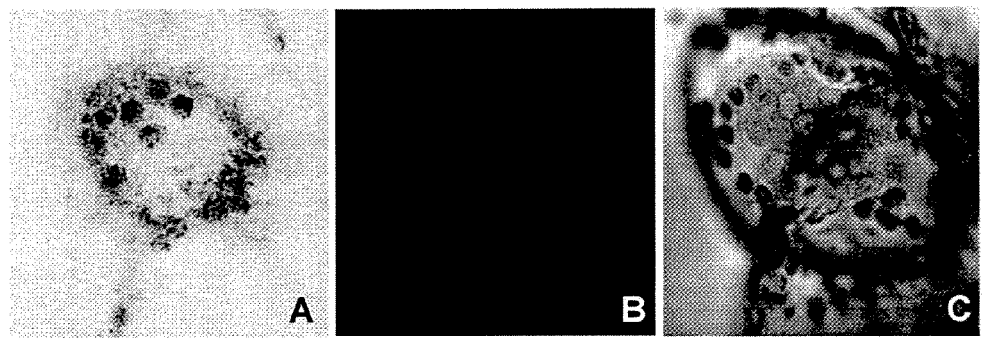
FIG. 6 shows reflectance and fluorescent microscopic images of cells containing nanoparticles. Panel A of FIG. 6 shows a reflectance image where the GNPs are preferentially seen. Panel B shows fluorescing particles within the background of red autofluorescing chloroplast. A merged reflectance and fluorescent image is shown in Panel C, wherein the yellow fluorescing particles are within the boundary of the chloroplast.

While the experiments done to track the particles within the chloroplast revealed that the particles appear to accumulate in the plastids, it was difficult to visually identify the presence of particles within the chloroplast envelope by using light microscopes, due to insufficient resolution. Thus, the particles were additionally tracked using reflectance and fluorescent microscopes, and the images were merged to clearly locate the particle, as seen in FIG. 6. Panel A of FIG. 6 shows a reflectance image where the GNPs are preferentially seen. This picture not only indicates the presence of nanoparticles in the chloroplast, but also shows heavy accumulation of the nanoparticles within chloroplast, indicating active uptake. Panel B shows fluorescing particles within the background of red autofluorescing chloroplast. A merged reflectance and fluorescent image is shown in Panel C, wherein the yellow fluorescing particles are within the boundary of the chloroplast, confirming the presence of the particle in the plastids.

Example 4

DNA Attached GNP Delivery for Nuclear Transformation

Figure 16:
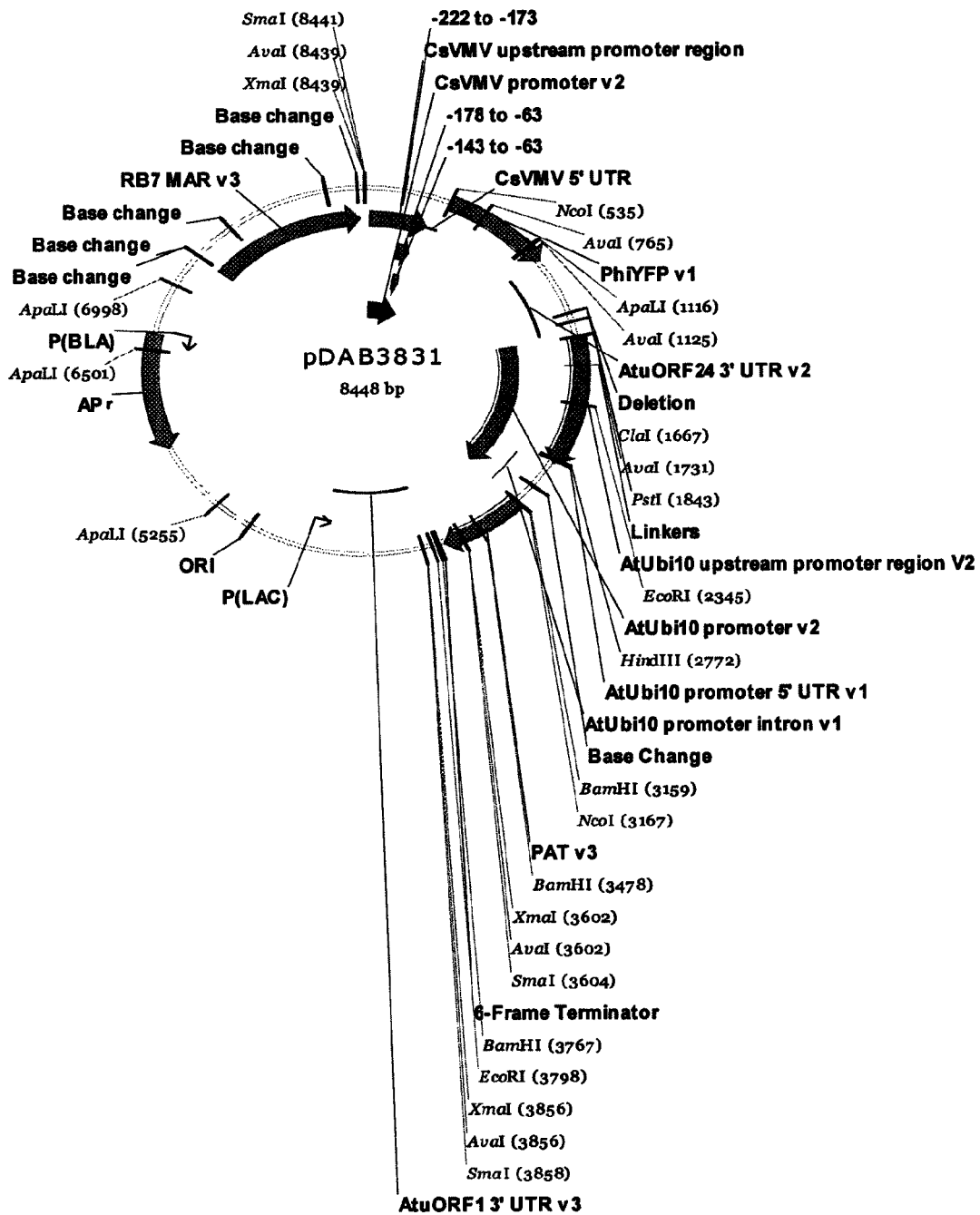
FIG. 16 shows Plasmid pDAB3831.

DNA coated GNPs were synthesized via 2 pathways i.e., non specific interaction and specific interaction (using PEG as a platform) and incubated with BY2/NT1 cells. For non specific interaction, 9 mL of 3% mannitol was added to 1 mL of cell suspension and then centrifuged for 5 minutes at 1000 rpm. The supernatant was then decanted and the cells resuspended in 300 μl of 3% mannitol. 50 μl of 150 nm diameter gold nanoparticles (available from BBI International (EM. GC150)) and 50 μg of plasmid DNA (pDAB3831) (FIG. 16) (SEQ. ID. NOS. 1 and 2) encoding YFP were added to the resuspended cells, and the mixture was allowed to incubate for 20 minutes. After incubation, 20 mL of 3% mannitol were added to the solution and the resulting mixture centrifuged for 5 minutes at 1000 rpms. The supernatant was then decanted and the cells resuspended in 3 mL growth media. The resuspended cells were then transferred to microwells for at least 48 hours before transfer to selection plates. For specific interaction (PEG pathway), a large excess equivalent of thiol ligand was used: 100 monolayers/particle, estimated by assuming that the occupied surface area by a single thiol molecule is ca. 0.20 nm. Using this calculation, 2 mg of SH-PEG(3)-OCH3 was added into the citrate GNPs solution. The mixture was rapidly stirred at room temperature for 20 h during which the color of the solution became slightly darker. Then, 3 volumes of THF were added to the reaction mixture and the resulting solution was centrifuged at 13 K rpm at 4° C. for 30 min. The supernatant was removed, the pellet was re-dissolved into 10 mL of ultra pure water (18 MΩ.cm), 30 mL of THF was added, and a second centrifugation in the same conditions was carried out. The pellet was then dissolved into ultra pure water (18 MΩ·cm) and kept at room temperature. To coat plasmid DNA onto $H_3CO$-PEG-5H-GNPs for transformation experiments, 1 mg of purified plasmid DNA was incubated with 10 mg gold particles in 50 ml water for 2 h at 23°. (see, Tomey, F. et al., Nature Nanotechnol. 2, (2007)).

Figure 7:
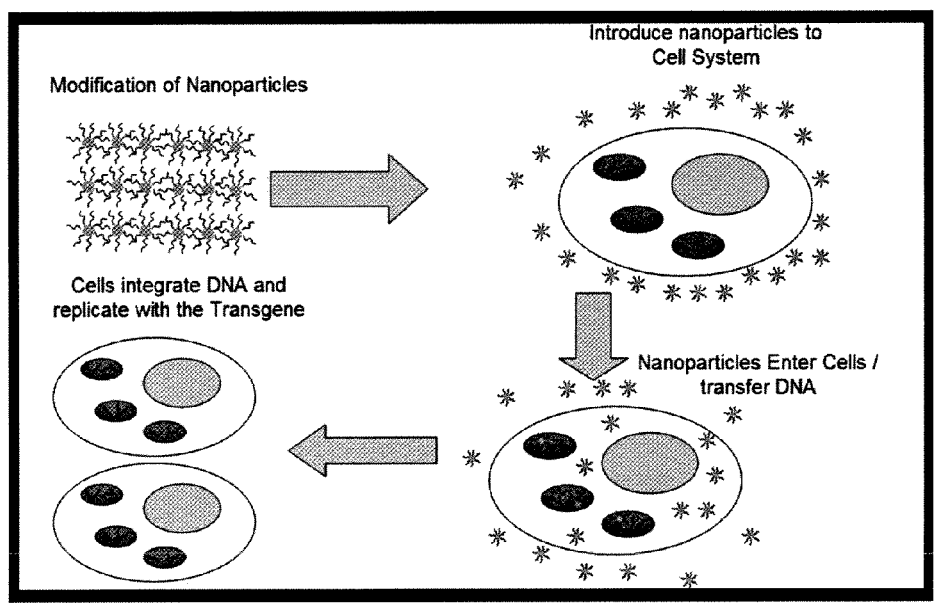
FIG. 7 shows a graphical representation of one possible transformation scheme according to an embodiment of the present invention.

A graphical representation of one possible transformation scheme is outlined in FIG. 7. For the transformation, a plasmid DNA, pDAB3831 comprising a YFP reporter gene was used. BY2 cells were treated as described supra and suspensions were incubated for 48 to 72 hrs with slow agitation in micro-well plates. A 50 μl aliquot of suspension was taken from the total 0.5-1 ml mixture and examined under a fluorescent microscope to observe for any expression of the reporter gene. BY2 cells transformed with the plasmid containing the YFP reporter gene showed transient expression of the YFP.

Example 5

DNA Attached PEGylated Quantum Dot Delivery for Nuclear Transformation

PEG functionalization of the QD for the cell entry evaluation studies: This protocol was adopted from Dubertret B, et.

al., Science 298, 1759 (2002)). 2 mg of TOPO (tri-octyl phosphine oxide)-coated CdSe/ZnS QDs (Ocean nanotechnology, Cat # QSO0630-0010) were suspended with 0.015 g (5.5 µmol) of PEG-PE (1,2-diacyl-sn-glycero-3-phosphoethanolamine-N—[methoxy-poly(ethylene glycol)]) (Avanti lipids, Cat #880160) in chloroform followed by evaporation of the solvent and solubilization with water. PEG conjugation was done to make sure that there is complete protection from cytotoxicity QD conjugation to plasmid DNA: 2 mg of TOPO (tri-octyl phosphine oxide)-coated QDs (Ocean nanotechnology, Cat # QS00630-0010) were suspended with 4 mg of HS-PEG-OCH$_3$ (Prochimia, Cat #TH 014-01) overnight at ~60-70° C. The solvent was removed in a vacuum oven. The residue was then suspended in 1 mL of water (18 M). The last step is accompanied by a change of the red residue to an orange, optically clear, transparent solution. To coat plasmid DNA onto H$_3$CO-PEG-5H-QDs for transformation experiments, 0.02 mg of purified plasmid DNA (pDAB 3831) was incubated with resultant QD conjugate in 2 ml of water for 2 h at 23° in dark. (Torney, F. et al., Nature Nanotechnol. 2, (2007)).

Incubation of QDs with tobacco intact cells: Experiments with cell lines were performed using Bright Yellow (BY2) tobacco single cell lines, maintained at 25° C. in LSBY2 medium. These single cell lines are produced by the same methodology outlined in IDM#64901. A concentration of 1-3 µL/mL was added to 500 µl of cells in a 24-well micro titer plate, and rotated on a shaker gently for 20 min before analyzing the cells.

Example 6

Nanoparticle Mediated Transduction and Cellular Internalization of Fluorescent Proteins into Intact Plant Cells and Potential Applications Materials to test nanoparticle mediation transduction and cellular internalization of proteins into plant cells include gold colloids of 150 nm diameter in size (BBI International, GC150), 5-((2-(and-3)-S (acetylmercapto)succinoyl)amino) fluorescein (SAMSA fluorescein: Invitrogen, A-685), nanoparticles of size 80 and 90 nm carboxylic acid coated gold Colloids (TedPella, 32019), Sulfo-NHS N-hydroxysulfosuccinimide), EDC(1-ethyl-3-[3-dimethylaminopropyl]carbodiimide hydrochloride), (Pierce Bitoechnology, 24510, 22980), MES (2-[N-morpholino]ethane sulfonic acid) (Fisher Scientific, AC32776-1000), Phosphate buffered saline buffer packets (Sigma, P5368-10PAK), Histdine tagged GFP (Evrogen, Excitation max—482 nm, Emission max—502 nm, FP611), turbo YFP (Evrogen, Excitation max—525 nm, Emission max—538 nm, FP611), and Propidium iodide (Sigma-P4864), Fluorescein diacetate (Sigma, F7378).

Cell cultures (BY2-E tobacco single cells): Both BY2 cells and NT1 cells were used. BY2/NT1 cells are a non-green, fast growing tobacco cell line. Three to four days prior to the experiments, a one-week-old suspension culture was subcultured to fresh medium by transfer of 2 ml of NT1 or BY2 culture into 40 ml NT1B or LSBY2 media containing 1 µl DAS-proprietary MTI-1 (PMTI-1) (a microtubule inhibitor), 1-3% Glycerol, and 0.05-0.1% (v/v) DMSO in a 250-mL flask. Single cells were collected either at 3.5 days or 7 days after the microtubule inhibitor treatment. The BY2 single cells used were processed through a Beckman Flow cytometer to count the viable cells. There were 658250 viable cells/ml with a mean diameter of 10.43 um (volume of 593.8 µm$^3$)-50.42 um (volume of 67079.05 µm$^3$). Live cells in these cultures, after PMTI-1 treatment, were all single cells. The cells were examined using a Differential Interference Contrast (DIC) microscope attached to a confocal fluorescence imaging system.

Nanoparticle conjugates: gold-fluorescein conjugate, gold-histidine tagged GFP conjugate, and gold-YFP conjugate were synthesized.

Synthesis of Gold-fluorescein conjugate: Gold-fluorescein conjugate was prepared by using a method described previously (Cannone, F., G. Chirico, et al. (2006), Quenching and Blinking of Fluorescence of a Single Dye Molecule Bound to Gold Nanoparticles. J. Phys. Chem. B 110(33): 16491-16498). 1 mg of SAMSA fluorescein was dissolved in 100 µl of 0.1 M NaOH and vortexed for 15 minutes to remove the acetyl group protecting the thiol. This activated SAMSA was mixed with 100 µl of 150 nm gold colloids (~10$^9$ particles/mil). This solution was then incubated for 1 hour to ensure the completion of the reaction. After incubation, 50 µL of 1M HCl was added to neutralize the solution. It was centrifuged at 3000 RPM for 30 minutes and supernatant was removed. The yellow pellet obtained was re-suspended in 200 µL of 0.1 M PBS, resulting in an orange colored solution. This purification step was repeated 2 times to ensure removal of free SAMSA fluorescein. The mode of attachment of SAMSA to gold is mainly via thiol bonding. Due to the significant electrostatic repulsion (SAMSA is dianionic at pH>7), SAMSA is believed to lie perpendicular to the gold colloidal surface (Cannone et. al. 2006).

Synthesis of Gold-histidine tagged GFP and Gold-YFP conjugate: Gold-protein conjugates were synthesized using a slight modification of protocol described by Grabarek (Grabarek, Z. and J. Gergely (1990), Zero-length cross linking procedure with the use of active esters. Analytical Biochemistry 185(1): 131-135)), which was illustrated for sequential coupling of two proteins. 0.25 ml of 90 nm carboxyl acid coated gold colloidal solution (~10$^9$ particles/ml) was centrifuged at 3000 RPM for 10 minutes. After discarding the supernatant, the red pellet was suspended in 1 ml of activation buffer (0.1 M MES, 0.5 M NaCl, pH 6.0). 0.4 mg EDC and 1.1 mg of sulfo-NHS was added to this solution and vortexed for 15 minutes at room temperature. Then, 9 µl of protein (histidine tagged GFP or turbo YFP) was added and the resulting solution was incubated for 2 hours in the dark at room temperature in order for the protein and gold to react completely. The ratio of gold colloids and protein used in this reaction was determined by finding the number of carboxylic acids present on gold colloids. First, number of carboxylic groups present on one gold colloid was calculated by dividing the surface area of 1 gold particle (sphere assumption) by surface occupied by one carboxylic group (0.20 nm$^2$ Kimura, K.; Takashima, S.; Ohshima, H. Journal of Physical Chemistry B 2002, 106, 7260-7266). This result was multiplied by total number of gold colloids present to obtain the total number of carboxylic groups present in entire gold colloidal solution. This was equated with the number of amino groups present in a given amount of protein. These gold colloids attach to protein via the formation of amide bond between carboxylic acid present on gold and amino group present on protein (Grabarek, Z. and J. Gergely (1990). Zero-length cross linking procedure with the use of active esters. Analytical Biochemistry 185(1): 131-135). There are roughly 127285 protein molecules tethered to one gold nanoparticle.

Cell treatments—Three separate samples were prepared for testing, as follows:

Time Course of Gold Uptake and Cell Viability—

The following samples were prepared in a 24 well sterile plates:

i) 500 µl of single BY2-E cells (control);

ii) 500 µl of single BY2-E cells+20 µl of GNP+25 µl of Fluorescein di-acetate (FDA)+25 µl of Propidium iodide; and iii) Other treatments include 40, 60, 80 μl of GNP with the cells and cell viability stains as mentioned above. Treated samples (Ref) were examined under fluorescence microscope at 5, 20, 120 min and finally after 18-20 hrs.

Gold-SAMSA Fluorescein Treatments—

The following samples were prepared in a 24 well sterile plates:
i) 500 μl of single BY2-E cells (control);
ii) 500 μl of single BY2-E cells+20 μl of SAMSA-fluorescein (control); and
iii) 500 μl of single BY2-E cells+20 μl of Au-SAMSA-fluorescein.

The treated cells were incubated for 20 minutes in dark at room temperature before conducting microscopy studies.

Gold-Histidine Tagged GFP Treatments—

The following samples were prepared in a 24 well sterile plates:
i) 500 μl of single BY2-E cells (control).
ii) 500 μl of single BY2-E cells+10 μl of histidine tagged GFP (control).
iii) 500 μl of single BY2-E cells+20 μl of Au-histidine tagged GFP.

The treated cells were incubated for 2 hours in dark at room temperature before conducting microscopy studies.

Microscopy: Phase contrast and Fluorescence microscopy of the single cell experiments with Au-SAMSA fluorescein and Au-histidine tagged GFP was carried out using Leica inverted fluorescence microscope (DAS). All the experiments were carried out at 20× magnification. FITC (fluorescein isothiocyanate) and GFP filter was used for SAMSA fluorescein and GFP single cell treatments respectively.

Differential Image Contrast (DIC), Confocal and Reflectance Microscopy:

These studies were carried out at UIUC (University of Illinois at Urbana Champaign) microscopy center on a Zeiss inverted microscope. For all these methods, the magnification was kept at 63×. For confocal, FITC, GFP and YFP filters were used for different cell treatments. For reflectance studies, dichroic mirror was replaced by a transparent glass slide and emission filter was removed.

Image Acquisition:

Suspension cultured tobacco cells were imaged using a Zeiss Axiovert M 200 microscope equipped with apotome optical sectioning system coupled with X-Cite 120 illumination system (Carl Zeiss microimaging, Obercohen, Germany). The gold particles were imaged under a reflectance imaging setup using the mercury illumination through 635/20 excitation filter and imaged using a IGS polarizing filter set (available from 33001, Chroma Technology Corp., Rockingham, Vt.) consisting of GG420 glass to block the UV, KG5 (IR blocker), 50/50 beam splitter and an excitation and emission parallel polarizers. Simultaneously, DIC/transmitted light images were acquired using standard DIC optics and the GFP in GFP-DNA coated gold particles were (psuedocolored green) acquired with a band pass FITC filter (HQ480/40 excitation filter, Q505LP dichroic mirror and HQ535/50 emission). Cells were aliquoted in a chambered cover glass setup having a thickness of 500 microns (Grace Bio-labs, Bend, Oreg.) for high resolution imaging. Most of the images were acquired with a 63×1.4 NA Planapochromat objective or with a 40×1.4 NA Planapochromat objective, depending on the cell size (available from Carl Zeiss Microimaging, Obercohen, Germany). Exposure times were set for each channel (i.e., DIC, Reflectance and/or FITC) and exposed sequentially using the Axiovision 4.6 program coupled with a high resolution Axiocam MRm monochrome camera (available from Carl Zeiss, Obercohen, Germany) with the dimension of 1388×1034 pixels. When needed, the resolution is set at 1024×1024 and a time lapse sequence of images obtained at the highest possible speed to resolve the particle dynamics over a period of 2-5 min consisting around 150-250 frames. The images were prepared either in the Axiovision 4.6 gallery module or Adobe Photoshop (Adobe Systems, San Jose, Calif.).

Time Course and GVP Internalization Studies:

To evaluate the impact of particle uptake and concentration of GNPs on cell intactness and viability, time course experiments were performed on BY2-E single cell lines incubated with citrate functionalized GNP (90 nm diameter). Various concentrations of GNP (20, 40, 60, 80 μl) were used in this experiment. The particles were internalized within 5 minutes after mixing with cells, while particle accumulation took up to 2 hrs to show increased levels in the cytosol and nucleus of the cells. Among the concentration tested, a higher level of cell viability and cell vigor was observed with 20 μl treatment as studied by FDA and PI (live/dead cell staining) protocol. In all the treated samples, the average viability of the cells was close to 98%, but with the highest concentration tested, no FDA stained nucleus was seen in 80 μl treatment. However, these unstained nuclei did not respond to PI, thus indicating no cell death. This result indicates the highest concentration of particle could lead to internal disturbances to an extent that the cell may be quiescent but still alive after 20 hrs after treatment.

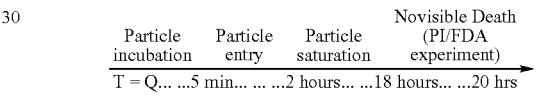

| Particle incubation | Particle entry | Particle saturation | Novisible Death (PI/FDA experiment) |
|---|---|---|---|
| T = Q... | ...5 min... | ...2 hours... | ...18 hours... ...20 hrs |

Figure 8:
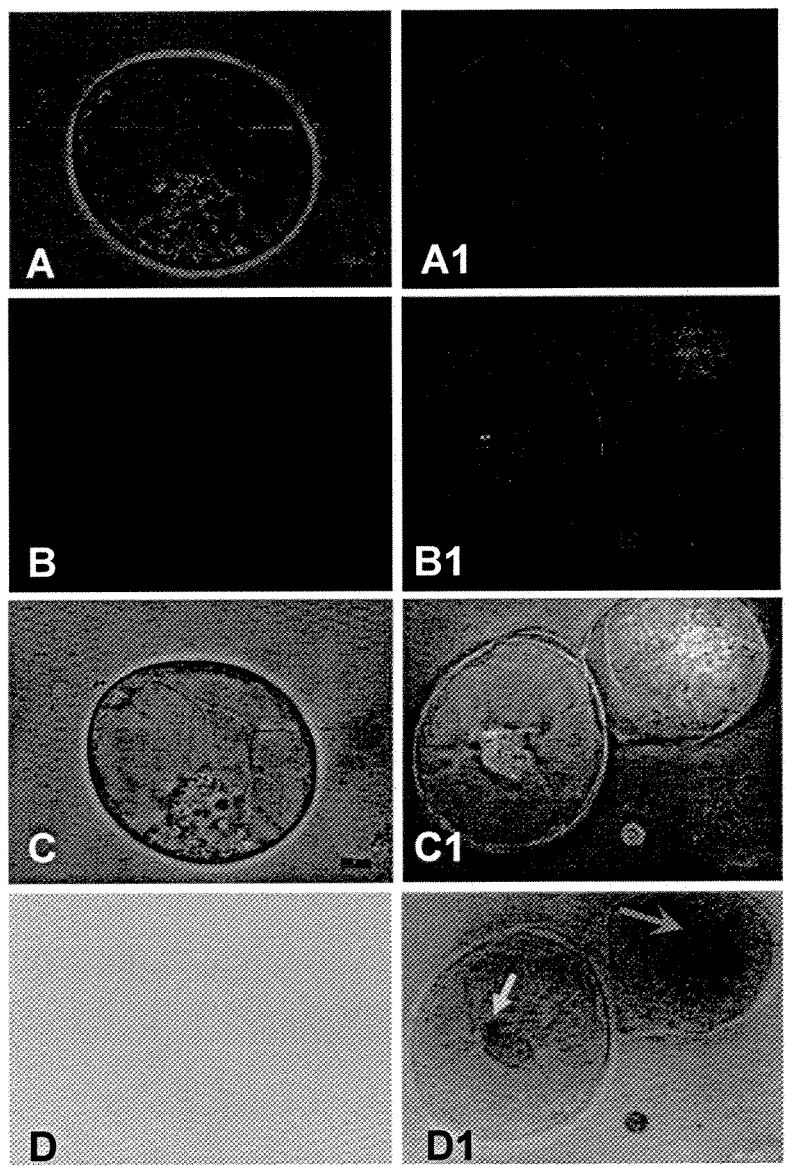
FIG. 8 shows cellular internalization of GFP as visualized through reflectance microscopy after two hours of treatment. Panels A and A1 show untreated control cells under DIC scope (Panel A), and GFP tethered Au-NP treated cells as seen under DIC scope (Panel A1); Panels B and B1 show control cells under reflectance scope (Panel B), and GFP tethered Au—NP treated cells as seen under reflectance scope (Panel B1), showing particle internalization from the reflected Au—NPs; Panels C and C1 show control cells superimposed images of DIC and reflectance scope (Panel C), and treated cells superimposed images of DIC and reflectance scope (Panel C1); Panels D and D1 show control cells reflectance inverted image to show no particle in the background (Panel D), and treated cells reflectance inverted image to show very clearly particle internalization (Panel D1).

Reflectance Microscope Tracking Studies:

Reflectance studies on single BY2/NT1 tobacco cells treated with gold Protein (GFP/YFP) conjugates show the presence of gold nanoparticles inside the cells. This was compared to untreated control single BY2 cells, which appeared to be dark under similar conditions, as shown in FIG. 8. Single gold nanoparticles emitting bright reflectance were observed, as shown in FIG. 8. This is a clear indication of uptake of gold nanoparticles by these walled BY2 cells.

Figure 9:
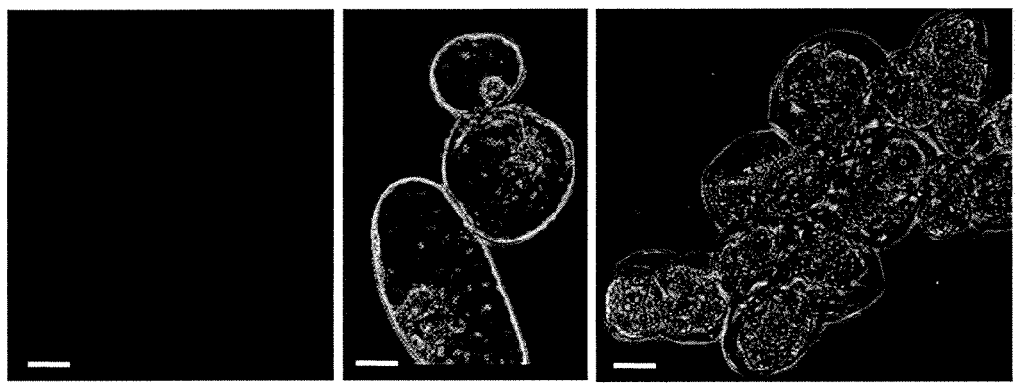
FIG. 9 shows SAMSA stain coated GNP internalization in Single cells. Panel A shows fluorescein stained single cells, with the cell wall and the medium showing fluorescence, but no internalization of stain; Panel B shows single cells under DIC scope; Panel C shows phase contrast imaging to show the nanoparticle (GNP 150 nm) internalization into the cytosol and the nucleus, with the fluorescein internalized only with the particle and the plasmalyzed cells under prolonged exposure up to 1 hr in the UV light.

Gold-SAMSA Fluorescein Experiments:

Phase contrast experiments conducted at DAS revealed a bright yellow staining of the intracellular space and nucleus for the treated cells as compared to silver contrast observed for control single cells. Also, in many cells, under conditions of plasmalysis, the plasma membrane withdrew itself from the cell wall, leaving a space in between indicating partial or complete plasmolysis of the cell, as shown in FIG. 9. Such cells, when observed under confocal fluorescence experiments of single cells treated with SAMSA fluorescein alone, showed fluorescence in the cytoplasm and the nucleus while it appeared to be dark in the untreated control cells. Also, the cells treated with SAMSA fluorescein stain alone showed some wall fluorescence, but not inside the cells. This means that SAMSA fluorescein is not internalized by the cells on its own and that the gold nanoparticle is acting like a carrier for its uptake.

Figure 10:
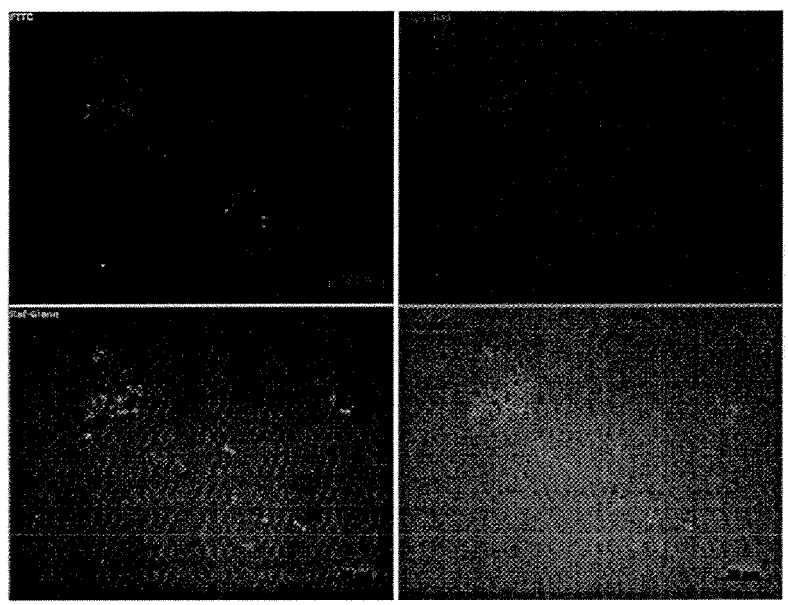
FIG. 10 shows Au-GFP conjugate with fluorescing GFP molecules, prior to mixing the single cells. Panel A (FITC), B (Brightfield), C (Reflectance), D (Panels A+B+C): GFP fluorescing Au-GNPs as observed through fluorescence microscopy, 2 hrs after incubation, but prior to mixing cells. Similar fluorescing particles could be seen on the particle showing reflectance in the nucleus (see FIG. 8).
Figure 11:
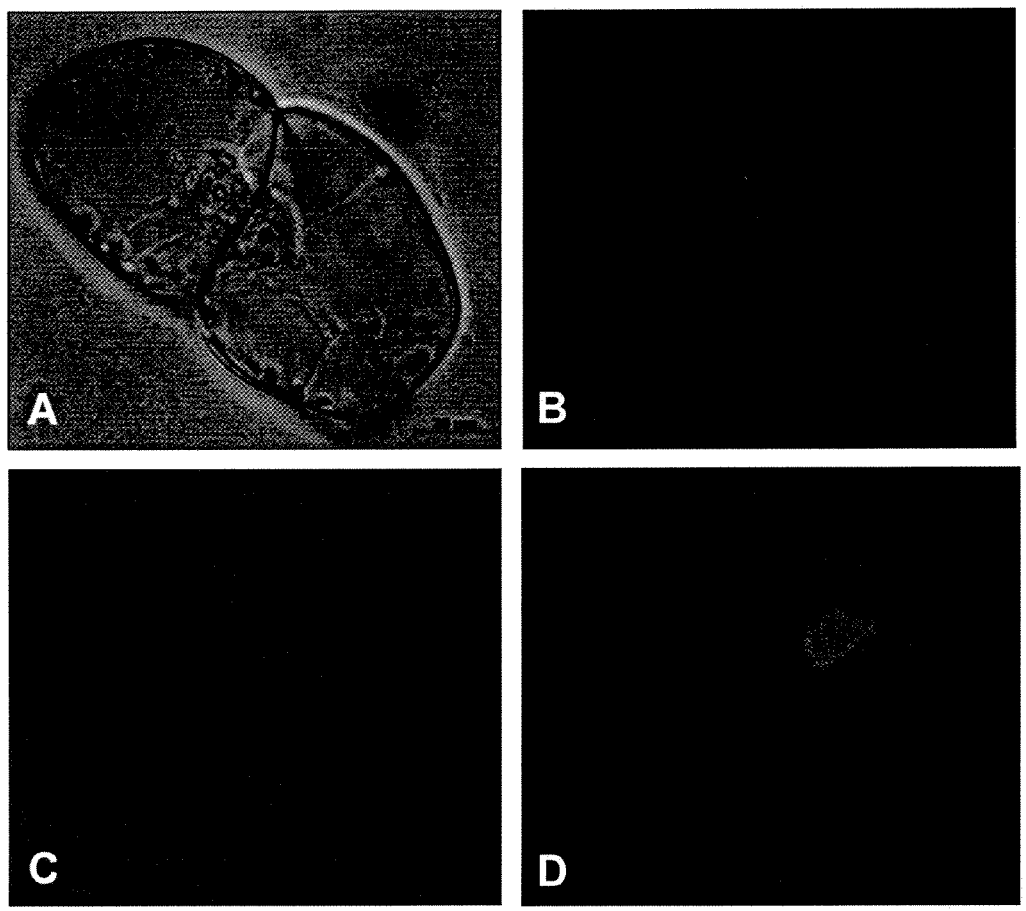
FIG. 11 shows nanoparticle (GNP 90 nm) mediated cellular internalization of GFP into BY2-E cell lines. Panel A shows dividing control cells with active cytoplasmic strands (Phase contrast image); Panel B shows the same cells as in Panel A when examined through FITC filter, where the autofluorescene from the nongreen plastids in the cytoplasm form the periphery and also from those plastids associated with the dividing nucleus; and where the cytoplasmic strands and the cytoplasm near the periphery of the cells do not show autofluorescence; Panel C shows control BY2 cells treated with GFP that are not attached to GNPs (FITC), where the cells do not show GFP uptake, but the GFP are surrounding the cells, but are not internalized; Panel D shows GNP mediated GFP internalization as observed through FITC filter, with the peripheral cytoplasm, cytoplasmic strands and the nucleus showing internalization of GFP as compared to the control in Panel B.
Figure 12:
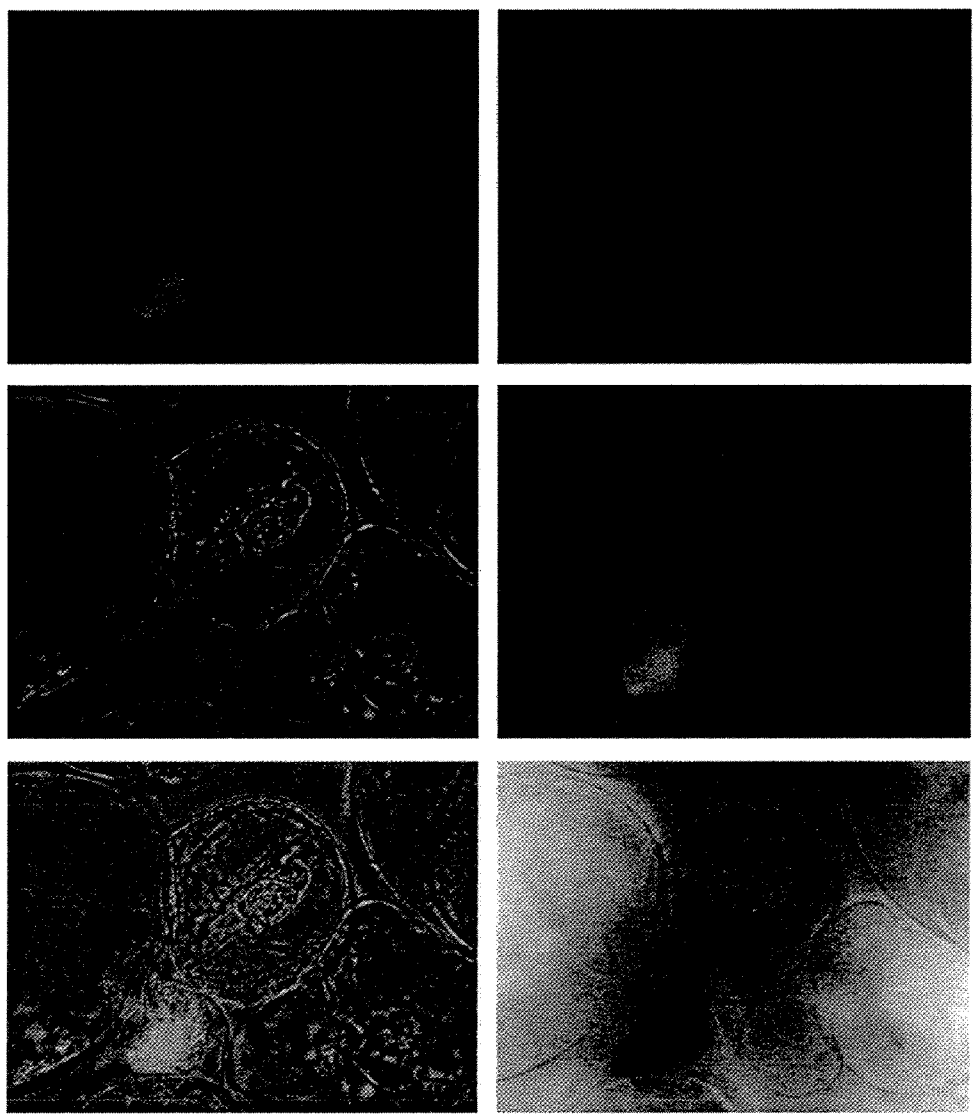
FIG. 12 shows BY2-E single cell lines showing GNP mediated YFP internalization 2 hrs after incubation of cells. Panel A (FITC), B (Rhodamine), C (DIC), D (Panels A+B), E (Panels A+B+C): F (Reflectance image inverted): YFP internalization as observed through fluorescence microscopy. Arrows in yellow show the internalization in a live single cell with YFP in the cytosol (diffused and concentrated in the nucleus). Arrows in orange show internalization in a plasmalyzed cells where the shrunk protoplast mass within the cell shows intense fluorescence indicating the YFP internalization in the cell. This cell is found in the same focal plane of the live cell that is placed adjacent, but below other live cells. The cells that accumulate a high level of particle and YFP fluorescence show cell death on prolonged examination under fluorescent scope.

Gold-Histidine Tagged GFP Experiments:

In order to establish the protein delivery to the intact cells via GNPs, we confirmed the GFP attachment to GNP using fluorescence microscopy, as shown in FIG. 10. Fluorescence images of BY2 cells treated with histidine tagged GFP show extracellular fluorescence with dark cells no fluorescence in the center. This indicates that in control treatments where histidine tagged GFP is added to the cells without Au particles do not internalize the particles. The evidence which support the intake of protein inside the cells were: i) increased fluorescence intensity of fluorescence in treated is cells internally, ii) fluorescing cytoplasmic strands in treated cells as compared to dark strands in control cells (see FIG. 11). Similar observations were made with YFP tethered GNPs, indicating the clear internalization of these fluorescent protein into the plant cells with intact cells (see FIG. 12).

There is a certain level of background reflectance and autofluorescence in the single cells that are inherent in plasmalyzing/dying or cells showing program cell death (PCD)-like cytological characteristics. In order to delineate the cells that have internalized the protein from such background problems and to unequivocally prove with the direct evidence for protein internalization, extensive reflectance scope investigation was carried out to focus and track individual particle or particle aggregate levels. The results of this study clearly showed internalization of particles with protein inside the cells and nucleus. However, the cells that accumulated increased number of particles with the fluorescent protein had a tendency to plasmalyze when observed under the microscope. It is likely that the increased concentration of protein due to the accumulation of high GNPs tethered to either GFP or YFP reaches toxic levels or the prolonged observation under the scope induces ROS which in turn has deleterious effect in such cells.

Example 7

Molecular Analysis and Proof for the Genomic Integration of Transgenes in the T1 Progeny of *Arabidopsis thaliana* cv Columbia Genomic DNA from *Arabidopsis* transgenic plants was extracted from total leaf material of 6-week-old using DNeasy Plant Mini kit according to the manufacturer's instructions (Qiagen Inc). The following YFP and PAT PCR primers were used to in the PCR reactions using the template genomic DNA from the T1 seedlings that tolerated 4-5× field level spray of Finale herbicide.

```
YFP
                                          (SEQ. ID. NO.3)
Forward Primer: 5'-TGTTCCACGGCAAGATCCCCTACG-3'

(SEQ. ID. NO.4)
Reverse Primer: 5'-TATTCATCTGGGTGTGATCGGCCA-3'

PAT
                                          (SEQ. ID. NO.5)
Forward Primer: 5'-GGAGAGGAGACCAGTTGAGATTAG-3'

(SEQ. ID. NO.6)
Reverse Primer: 5'-AGATCTGGGTAACTGGCCTAACTG-3'
```

Figure 13:
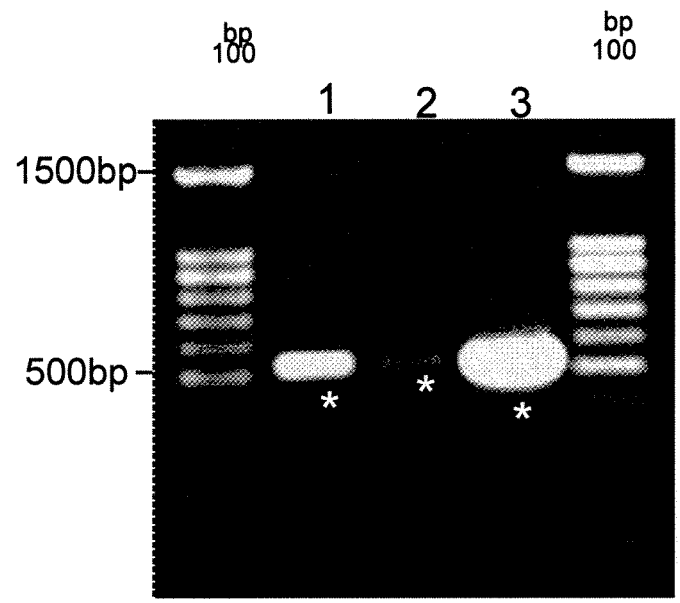
FIGS. 13 and 14 show gel images of PAT and YFP amplified gene products were amplified.
Figure 14:
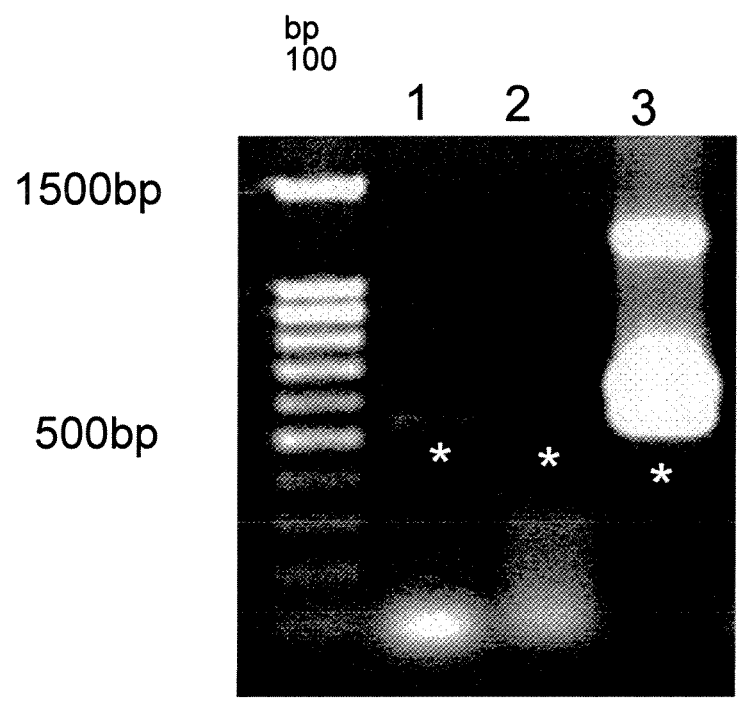

The PCR for PAT and YFP (Yellow Florescent tag, Evrogen) gene products were amplified in total reaction volume 50 µL of the mixture containing 100 ng genomic template DNA, 1×ExTaq reaction buffer (TaKaRa Bio), 0.2 mM dNTP, 10 µmol each primer, and 0.025 units/µL ExTaq. The following PCR conditions were used: 1 cycle at 96° C. for 5 min and 31 cycles of the following PCR program: 94° C., 15 s; 65° C., 30 s; 72° C., 1 min. and final extension was performed at 72° C. for 7 min to complete product synthesis. The gel images were obtained using Bio Rad Gel imagining System. (FIGS. 13 and 14). The amplified fragments were gel-purified using a gel purification kit (Qiagen Inc) according to the manufacturer's instructions The PCR fragments were sequenced using PAT forward primer and YFP forward at using advanced Sanger sequencing technology (MWG Biotechnologies, Inc) and the sequence was analyzed using Sequencher software.

The results show that the PAT and YFP sequences were delivered through the nanoparticle and Quantum dot mediated DNA delivery, thus providing clear evidence of stable genomic integration of transgenes in the genomic DNA of the T1 plants.

Example 8

Facilitated Delivery of QD Across the JTNT1 Tobacco Single Cell Wall

Several peptides were surface functionalized based on the procedure discussed in Example 7 to test the noninvasive delivery of the QDs across the cell wall. Cell Penetrating Peptide (CPP)/Protein Transduction unit (PTD) attachment determination was carried out via gel electrophoresis as described below.

Figure 15:
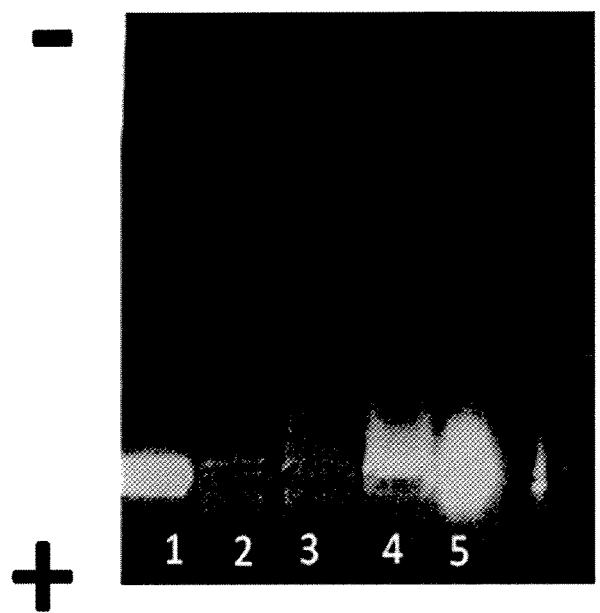
FIG. 15 shows gel electrophoresis carried out on QD-peptide conjugates to confirm the attachment of peptides to QDs.

Gel electrophoresis was carried out on QD-peptide conjugates to confirm the attachment of peptides to QDs. The samples used were QD-Amine (control), QD-Amine-R9, QD-Amine-Zein, QD-Amine-Pep1 and QD-Amine-MPG. R9, Zein, Pep1 and MPG are peptides. A 2% (w/v) agarose gel was run at 120 V in TBE (1×, pH 8) buffer for 1 hour. The QD-Amine-peptides migrated towards the negative end of the electrode showing the attachment of strongly positive character of the peptides attached to QDs while QD-Amine remained static showing weak positive charge of the amine group due to the neutralizing effect of gel buffer at a basic Ph, as shown in FIG. 15 (Lane 1: QD-Amine; 2: QD Amine-R9; 3: QD-Amine-Y-Zein; 4: QD Amine-Pep1; 5: QD-Amine-MPG).

The peptides were tested for internalization into the cells and the emission of QD inside the cell was used as a measure to track the level of internalization of the particles inside the cell and compartments. JTNT1 single cells with intact walls were used as target cells in these experiments. Table 1 shows the treatments of the samples. The cells were tracked under the scope.

Microscopy was carried out within 1 minute after the preparation of the sample on Spinning Disk Confocal microscope (Andor Technology Revolution System). The excitation filter was set at 488 nm while the emission filter was set beyond 650 nm.

As shown in Table 1, the control protoplasts and JTNT1 showed no auto fluorescence at the emission wavelength used for QDs. Significant debris (broken cell parts) was observed in each of these samples. Samples 4, 5, 6, and 7 did not show internalization of QDs inside single cells or protoplasts. Sample 8 and 9 indicated a clear presence of QDs surrounding the nucleus in both walled single cells and protoplasts. This was due to the presence of the cell penetrating peptide on the QDs which has the nuclear localization signal (NLS). However, sample #6 and 7 had γ-Zein tethered to the QDs showed no QD internalization inside the cell. This indicates that the QDs were taken into the cells due to the Cell Penetrating Peptide (CPP) or the Protein Transduction unit (PTD), γ-Zein as the QDs that were functionalized only with amine and not CPP/PTD did not get internalized.

TABLE 1

| | Functionalization type | Single Cell type used (100 ul) | Functionalized QD volume | Autofluorescence 480-650 nm | QD localization in the cell |
|---|---|---|---|---|---|
| 1 | QD-PEG-Amine-Control-1 | NA | 20 ul | No | NA |
| 2 | Protoplast -Control-2 | Tobacco JTNT1 protoplast | 0 ul | No | NA |
| 3 | Single cells (Control-3) | Tobacco JTNT1 walled single cells | 0 ul | No | NA |
| 4 | QD-PEG-Amine | Tobacco JTNT1 protoplast | 20 ul | No | No |
| 5 | QD-PEG-Amine | Tobacco JTNT1 walled single cells | 20 ul | No | No |
| 6 | QD-PEG-Amine-Zein | Tobacco JTNT1 protoplast | 20 ul | No | No |
| 7 | QD-PEG-Amine-Zein | Tobacco JTNT1 walled single cells | 20 ul | No | No |
| 8 | QD-Amine-y-Zein | Tobacco JTNT1 protoplast | 20 ul | No | Yes |
| 9 | QD-Amine-y-Zein | Tobacco JTNT1 walled single cells | 20 ul | No | Yes |

This data demonstrates evidence of cell internalization of Quantum dots tethered to CPP/PTD with the nuclear localization signal (NLS) taking the QDs across the cell wall of the intact functional cell via Spinning Disk Confocal microscope (Andor Technology Revolution System). The nuclear localization of the QDs is possible across the cell wall in sample 9 and in the absence of the cell wall as seen the protoplast based cell internalization that is relieved of a cell wall through enzyme treatment. Thus the mere presence of the cell wall does not hinder the internalization of Quantum dots, evidencing particle entry is demonstrated non-invasively with a CPP/PTD in plant cells with intact cell wall.

Wile this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims and their equivalents.

What may be claimed is:

1. A method of introducing a molecule of interest into a plant cell having a cell wall, the method comprising:
   providing the plant cell having a cell wall;
   coating a nanoparticle with a nucleic acid molecule of interest, wherein the nanoparticle is a gold nanoparticle or quantum dot;
   coating the nanoparticle with a subcellular compartment targeting protein;
   placing the cell having a cell wall and the coated nanoparticle in contact with each other; and
   allowing uptake of the nanoparticle and the molecule of interest into the cell comprising a cell wall.

2. The method according to claim 1, wherein coating a nanoparticle with a nucleic acid molecule of interest comprises immobilizing the nucleic acid molecule of interest via noncovalent absorption on the surface of the nanoparticle.

3. The method according to claim 1, further comprising absorbing the nucleic acid molecule of interest into the nanoparticle.

4. The method according to claim 1, further comprising allowing uptake of the nanoparticle into a compartment of the plant cell comprising a cell wall.

5. The method according to claim 1, wherein the subcellular compartment targeting protein targets the nanoparticle to a plastid.

6. The method according to claim 1, wherein the plant cell comprising a cell wall is selected from the group consisting of tobacco, carrot, maize, canola, rapeseed, cotton, palm, peanut, soybean, *Oryza* sp., *Arabidopsis* sp., *Ricinus* sp., and sugarcane cells.

7. The method according to claim 1, wherein the plant cell is from a tissue selected from the group consisting of embryo, meristematic, callus, pollen, leaves, anthers, roots, root tips, flowers, seeds, pods and stems.

8. The method according to claim 1, further comprising derivatizing the surface of the nanoparticle.

9. The method according to claim 1, wherein the nucleic acid molecule of interest comprises a gene.

10. The method according to claim 9, wherein the gene is a foreign protein gene, an agronomic gene, or a marker gene.

11. The method according to claim 1, further comprising selecting cells that have stably integrated the molecule of interest.

12. The method according to claim 11, wherein the selected cells are regenerable cells.

13. The method according to claim 12, further comprising regenerating a plant from the selected cells.

14. A method of introducing a molecule of interest into a plant cell having a cell wall, the method comprising:
   providing the plant cell having a cell wall;
   coating a nanoparticle selected from the group consisting of gold nanoparticles, gold coated nanoparticles, and quantum dots, with a nucleic acid molecule of interest;
   coating the nanoparticle with a protein capable of targeting the nanoparticle to a subcellular compartment;
   placing the cell having a cell wall and the coated nanoparticle in contact with each other; and
   allowing uptake of the nanoparticle and the molecule of interest into the cell comprising a cell wall.

15. The method according to claim 14, wherein coating the nanoparticle with the nucleic acid molecule of interest comprises immobilizing the molecule of interest via noncovalent absorption on the surface of the nanoparticle.

16. The method according to claim 14, further comprising absorbing the nucleic acid molecule of interest into the nanoparticle.

17. The method according to claim 14, wherein the subcellular compartment targeting protein targets the nanoparticle to a plastid.

18. The method according to claim 14, wherein the plant cell comprising a cell wall is selected from the group consisting of tobacco, carrot, maize, canola, rapeseed, cotton, palm, peanut, soybean, *Oryza* sp., *Arabidopsis* sp., *Ricinus* sp., and sugarcane cells.

19. The method according to claim 14, wherein the plant cell is from a tissue selected from the group consisting of embryo, meristematic, callus, pollen, leaves, anthers, roots, root tips, flowers, seeds, pods and stems.

20. The method according to claim 14, further comprising derivatizing the surface of the nanoparticle.

21. The method according to claim 14, wherein the nucleic acid molecule of interest comprises a gene.

22. The method according to claim 21, wherein the gene is a foreign protein gene, an agronomic gene, or a marker gene.

23. The method according to claim 14, further comprising selecting cells that have stably integrated the molecule of interest.

24. The method according to claim 23, wherein the selected cells are regenerable cells.

25. The method according to claim 24, further comprising regenerating a plant from the selected cells.

\* \* \* \* \*

SEQUENCE LISTING

```
<160> NUMBER OF SEQ ID NOS: 6

<210> SEQ ID NO 1
<211> LENGTH: 8448
<212> TYPE: DNA
<213> ORGANISM: Artificial Sequence
<220> FEATURE:
<223> OTHER INFORMATION: Plasmid pDAB3831

<400> SEQUENCE: 1
ggccgctaaa cccagaaggt aattatccaa gatgtagcat caagaatcca atgtttacgg      60
gaaaaactat ggaagtatta tgtaagctca gcaagaagca gatcaatatg cggcacatat     120
gcaacctatg ttcaaaaatg aagaatgtac agatacaaga tcctatactg ccagaatacg     180
aagaagaata cgtagaaatt gaaaagaag aaccaggcga agaaaagaat cttgaagacg     240
taagcactga cgacaacaat gaaaagaaga agataaggtc ggtgattgtg aaagagacat     300
agaggacaca tgtaaggtgg aaaatgtaag ggcggaaagt aaccttatca caaggaatc     360 ttatccccca ctacttatcc ttttatattt ttccgtgtca tttttgccct tgagttttcc     420
tatataagga accaagttcg gcatttgtga aaacaagaaa aaatttggtg taagctattt     480
tctttgaagt actgaggata caacttcaga gaaatttgta agtttgtaga tctccatggg     540
ctccagcggc gccctgctgt tccacggcaa gatcccctac gtggtggaga tggagggcaa     600
tgtggatggc cacaccttca gcatccgcgg caagggctac ggcgatgcca gcgtgggcaa     660
ggtggatgcc cagttcatct gcaccaccgg cgatgtgccc gtgccctgga gcaccctggt     720
gaccaccctg acctacggcg cccagtgctt cgccaagtac ggccccgagc tgaaggattt     780
ctacaagagc tgcatgccgg atggctacgt gcaggagcgc accatcacct tcgagggcga     840
tggcaatttc aagacccgcg ccgaggtgac cttcgagaat ggcagcgtgt acaatcgcgt     900
```

```
gaagctgaat ggccagggct tcaagaagga tggccacgtg ctgggcaaga atctggagtt    960
caatttcacc ccccactgcc tgtacatctg gggcgatcag gccaatcacg gcctgaagag   1020
cgccttcaag atctgccacg agatcaccgg cagcaagggc gatttcatcg tggccgatca   1080
cacccagatg aataccccca tcggcggcgg ccccgtgcac gtgcccgagt accaccacat   1140
gagctaccac gtgaagctga gcaaggatgt gaccgatcac cgcgataata tgagcctgaa   1200
ggagaccgtg cgcgccgtgg attgccgcaa gacctacctg tgagagctcg catgcggtca   1260
ccaaaccttg gactcccatg ttggcaaagg caaccaaaca aacaatgaat gatccgctcc   1320
tgcatatggg gcggtttgag tatttcaact gccatttggg ctgaattgaa gacatgctcc   1380
tgtcagaaat tccgtgatct tactcaatat tcagtaatct cggccaatat cctaaatgtg   1440
cgtggcttta tctgtctttg tattgtttca tcaattcatg taacgtttgc ttttcatatg   1500
aattttcaaa taaattatcg cgatagtact acgaatattt cgtatcgctg atcttctcaa   1560
tcacaatgat gcgtagtgac ccgacaaata atttaagcgt ccttaatacc aatcctaaaa   1620
taattgaggc aaataaaatt ttttgtaat ttttatgata gcagatcgat tctccagcaa   1680
gcctgcaaca aaatattgtg tatttctaaa tagattttga tattaaaatc ccgagaaagc   1740
aaaattgcat ttaacaaaac agtaatttag tacattaata aaaattatgc tcggccggcc   1800
gcggccgctt aattaaattt aaatgtttaa accccgcctg caggtcaacg gatcaggata   1860
ttcttgttta agatgttgaa ctctatggag gtttgtatga actgatgatc taggaccgga   1920
taagttccct tcttcatagc gaacttattc aaagaatgtt ttgtgtatca ttcttgttac   1980
attgttatta atgaaaaaat attattggtc attggactga acacgagtgt taaatatgga   2040
ccaggcccca aataagatcc attgatatat gaattaaata acaagaataa atcgagtcac   2100
caaaccactt gccttttta acgagacttg ttcaccaact tgatacaaaa gtcattatcc   2160
tatgcaaatc aataatcata caaaaatatc caataacact aaaaaattaa aagaaatgga   2220
taatttcaca atatgttata cgataaagaa gttacttttc caagaaattc actgatttta   2280
taagcccact tgcattagat aaatggcaaa aaaaacaaa aaggaaaaga aataaagcac   2340
gaagaattct agaaaatacg aaatacgctt caatgcagtg ggacccacgg ttcaattatt   2400
gccaattttc agctccaccg tatatttaaa aaataaaacg ataatgctaa aaaaatataa   2460
atcgtaacga tcgttaaatc tcaacggctg gatcttatga cgaccgttag aaattgtggt   2520
tgtcgacgag tcagtaataa acggcgtcaa agtggttgca gccggcacac acgagtcgtg   2580
tttatcaact caaagcacaa atacttttcc tcaacctaaa aataaggcaa ttagccaaaa   2640
acaactttgc gtgtaaacaa cgctcaatac acgtgtcatt ttattattag ctattgcttc   2700
accgccttag ctttctcgtg acctagtcgt cctcgtcttt tcttcttctt cttctataaa   2760
acaatacca aagcttcttc ttcacaattc agatttcaat ttctcaaaat cttaaaaact   2820
ttctctcaat tctctctacc gtgatcaagg taaatttctg tgttccttat tctctcaaaa   2880
tcttcgattt tgtttcgtt cgatcccaat ttcgtatatg ttctttggtt tagattctgt   2940
taatcttaga tcgaagacga ttttctgggt ttgatcgtta gatatcatct taattctcga   3000
ttagggtttc ataaatatca tccgatttgt tcaaataatt tgagttttgt cgaataatta   3060
ctcttcgatt tgtgatttct atctagatct ggtgttagtt tctagtttgt gcgatcgaat   3120
ttgtcgatta atctgagttt ttctgattaa caggtaagga tccaaccatg gcttctccgg   3180
agaggagacc agttgagatt aggccagcta cagcagctga tatggccgcg gtttgtgata   3240
tcgttaacca ttacattgag acgtctacag tgaactttag gacagagcca caaacaccac   3300
```

```
aagagtggat tgatgatcta gagaggttgc aagatagata cccttggttg gttgctgagg    3360
ttgagggtgt tgtggctggt attgcttacg ctgggccctg gaaggctagg aacgcttacg    3420
attggacagt tgagagtact gtttacgtgt cacataggca tcaaaggttg ggcctaggat    3480
ccacattgta cacacatttg cttaagtcta tggaggcgca aggttttaag tctgtggttg    3540
ctgttatagg ccttccaaac gatccatctg ttaggttgca tgaggctttg ggatacacag    3600
cccggggtac attgcgcgca gctggataca agcatggtgg atggcatgat gttggttttt    3660
ggcaaaggga ttttgagttg ccagctcctc caaggccagt taggccagtt acccagatct    3720
gaggtaccct gagcttgagc ttatgagctt atgagcttag agctcggatc cactagtaac    3780
ggccgccagt gtgctggaat tcgcccttga ctagataggc gcccagatcg gcggcaatag    3840
cttcttagcg ccatcccggg ttgatcctat ctgtgttgaa atagttgcgg tgggcaaggc    3900
tctctttcag aaagacaggc ggccaaagga acccaaggtg aggtgggcta tggctctcag    3960
ttccttgtgg aagcgcttgg tctaaggtgc agaggtgtta gcgggatgaa gcaaaagtgt    4020
ccgattgtaa caagatatgt tgatcctacg taaggatatt aaagtatgta ttcatcacta    4080
atataatcag tgtattccaa tatgtactac gatttccaat gtctttattg tcgccgtatg    4140
taatcggcgt cacaaaataa tccccggtga cttctcttta atccaggatg aaataatatg    4200
ttattataat ttttgcgatt tggtccgtta taggaattga agtgtgcttg cggtcgccac    4260
cactcccatt tcataatttt acatgtattt gaaaaataaa aatttatggt attcaattta    4320
aacacgtata cttgtaaaga atgatatctt gaaagaaata tagtttaaat atttattgat    4380
aaaataacaa gtcaggtatt atagtccaag caaaaacata aatttattga tgcaagttta    4440
aattcagaaa tatttcaata actgattata tcagctggta cattgccgta gatgaaaagac   4500 tgagtgcgat attatggtgt aatacatagc ggccgggttt ctagtcaccg tgtagcttg    4560 gcgtaatcat ggtcatagct gtttcctgtg tgaaattgtt atccgctcac aattccacac    4620
aacatacgag ccggaagcat aaagtgtaaa gcctggggtg cctaatgagt gagctaactc    4680
acattaattg cgttgcgctc actgcccgct ttccagtcgg gaaacctgtc gtgccagctg    4740
cattaatgaa tcggccaacg cgcggggaga ggcggtttgc gtattgggcg ctcttccgct    4800
gcgcacgctg cgcacgctgc gcacgcttcc tcgctcactg actcgctgcg ctcggtcgtt    4860
cggctgcggc gagcggtatc agctcactca aaggcggtaa tacggttatc cacagaatca    4920
ggggataacg caggaaagaa catgtgagca aaaggccagc aaaaggccag gaaccgtaaa    4980
aaggccgcgt tgctggcgtt tttccatagg ctccgccccc ctgacgagca tcacaaaaat    5040
cgacgctcaa gtcagaggtg gcgaaacccg acaggactat aaagatacca ggcgtttccc    5100
cctggaagct ccctcgtgcg ctctcctgtt ccgaccctgc cgcttaccgg atacctgtcc    5160
gcctttctcc cttcgggaag cgtggcgctt tctcatagct cacgctgtag gtatctcagt    5220
tcggtgtagg tcgttcgctc caagctgggc tgtgtgcacg aacccccgt tcagcccgac    5280 cgctgcgcct tatccggtaa ctatcgtctt gagtccaacc cggtaagaca cgacttatcg    5340
ccactggcag cagccactgg taacaggatt agcagagcga ggtatgtagg cggtgctaca    5400
gagttcttga agtggtggcc taactacggc tacactagaa ggacagtatt tggtatctgc    5460
gctctgctga agccagttac cttcggaaaa agagttggta gctcttgatc cggcaaacaa    5520
accaccgctg gtagcggtgg tttttttgtt tgcaagcagc agattacgcg cagaaaaaaa    5580
ggatctcaag aagatccttt gatcttttct acggggtctg acgctcagtg gaacgaaaac    5640
tcacgttaag ggattttggt catgagatta tcaaaaagga tcttcaccta gatccttta    5700
```

```
aattaaaaat gaagttttaa atcaatctaa agtatatatg agtaaacttg gtctgacagt    5760
taccaatgct taatcagtga ggcacctatc tcagcgatct gtctatttcg ttcatccata    5820
gttgcctgac tccccgtcgt gtagataact acgatacggg agggcttacc atctggcccc    5880
agtgctgcaa tgataccgcg agacccacgc tcaccggctc cagatttatc agcaataaac    5940
cagccagccg gaagggccga gcgcagaagt ggtcctgcaa ctttatccgc ctccatccag    6000
tctattaatt gttgccggga agctagagta agtagttcgc cagttaatag tttgcgcaac    6060
gttgttgcca ttgctacagg catcgtggtc tcacgctcgt cgtttggtat ggcttcattc    6120
agctccggtt cccaacgatc aaggcgagtt acatgatccc ccatgttgtg caaaaaagcg    6180
gttagctcct tcggtcctcc gatcgttgtc agaagtaagt tggccgcagt gttatcactc    6240
atggttatgg cagcactgca taattctctt actgtcatgc catccgtaag atgcttttct    6300
gtgactggtg agtactcaac caagtcattc tgagaatagt gtatgcggcg accgagttgc    6360
tcttgcccgg cgtcaatacg ggataatacc gcgccacata gcagaacttt aaaagtgctc    6420
atcattggaa aacgttcttc ggggcgaaaa ctctcaagga tcttaccgct gttgagatcc    6480
agttcgatgt aacccactcg tgcacccaac tgatcttcag catctttac tttcaccagc    6540 gtttctgggt gagcaaaaac aggaaggcaa atgccgcaa aaagggaat aagggcgaca    6600 cggaaatgtt gaatactcat actcttcctt tttcaatatt attgaagcat ttatcagggt    6660
tattgtctca tgagcggata catatttgaa tgtatttaga aaataaaca aatagggggtt    6720 ccgcgcacat ttccccgaaa agtgccacct gacgtctaag aaaccattat tatcatgaca    6780
ttaacctata aaaataggcg tatcacgagg ccctttcgtc tcgcgcgttt cggtgatgac    6840
ggtgaaaacc tctgacacat gcagctcccg gagacggtca cagcttgtct gtaagcggat    6900
gccgggagca gacaagcccg tcagggcgcg tcagcgggtg ttggcgggtg tcggggctgg    6960
cttaactatg cggcatcaga gcagattgta ctgagagtgc accatatgcg gtgtgaaata    7020
ccgcacagat gcgtaaggag aaaataccgc atcaggcgcc attcgccatt caggctgcgc    7080
aactgttggg aagggcgatc ggtgcgggcc tcttcgctat tacgccagct ggcgaaaggg    7140
ggatgtgctg caaggcgatt aagttgggta acgccagggt ttttcccagtc acgacgttgt    7200 aaaacgacgg ccagtgaatt acaccggtgt gatcatgggc cgcgattaaa aatctcaatt    7260
atatttggtc taatttagtt tggtattgag taaaacaaat tcgaaccaaa ccaaaatata    7320
aatatatagt ttttatatat atgcctttaa gacttttat agaattttct ttaaaaaata    7380
tctagaaata tttgcgactc ttctggcatg taatatttcg ttaaatatga agtgctccat    7440
ttttattaac tttaaataat tggttgtacg atcacttct tatcaagtgt tactaaaatg    7500
cgtcaatctc tttgttcttc catattcata tgtcaaaacc tatcaaaatt cttatatatc    7560
tttttcgaat ttgaagtgaa atttcgataa tttaaaatta aatagaacat atcattattt    7620
aggtatcata ttgatttta tacttaatta ctaaatttgg ttaactttga agtgtacat    7680 caacgaaaaa ttagtcaaac gactaaaata aataaatatc atgtgttatt aagaaaattc    7740
tcctataaga atatttaat agatcatatg tttgtaaaaa aaattaattt ttactaacac    7800
atatatttac ttatcaaaaa tttgacaaag taagattaaa ataatattca tctaacaaaa    7860
aaaaaaccag aaaatgctga aaacccggca aaaccgaacc aatccaaacc gatatagttg    7920
gtttggtttg atttgatat aaaccgaacc aactcggtcc atttgcaccc ctaatcataa    7980
tagctttaat atttcaagat attattaagt taacgttgtc aatatcctgg aaattttgca    8040
aaatgaatca agcctatatg gctgtaatat gaatttaaaa gcagctcgat gtggtggtaa    8100
```

| | |
|---|---|
| tatgtaattt acttgattct aaaaaaatat cccaagtatt aataatttct gctaggaaga | 8160 |
| aggttagcta cgatttacag caaagccaga atacaatgaa ccataaagtg attgaagctc | 8220 |
| gaaatatacg aaggaacaaa tattttttaaa aaaatacgca atgacttgga acaaaagaaa | 8280 |
| gtgatatatt ttttgttctt aaacaagcat cccctctaaa gaatggcagt tttcctttgc | 8340 |
| atgtaactat tatgctccct tcgttacaaa aattttggac tactattggg aacttcttct | 8400 |
| gaaaatagtg gccaccgctt aattaaggcg cgccatgccc gggcaagc | 8448 |

<210> SEQ ID NO 2
<211> LENGTH: 8448
<212> TYPE: DNA
<213> ORGANISM: Artificial sequence
<220> FEATURE:
<223> OTHER INFORMATION: reverse complement of SEQ ID NO: 1

<400> SEQUENCE: 2

| | |
|---|---|
| gcttgcccgg gcatggcgcg ccttaattaa gcggtggcca ctattttcag aagaagttcc | 60 |
| caatagtagt ccaaaatttt tgtaacgaag ggagcataat agttacatgc aaaggaaaac | 120 |
| tgccattctt tagaggggat gcttgttaa gaacaaaaaa tatatcactt tcttttgttc | 180 |
| caagtcattg cgtattttt taaaaatatt tgttccttcg tatatttcga gcttcaatca | 240 |
| ctttatggtt cattgtattc tggctttgct gtaaatcgta gctaaccttc ttcctagcag | 300 |
| aaattattaa tacttgggat attttttag aatcaagtaa attacatatt accaccacat | 360 |
| cgagctgctt ttaaattcat attacagcca tataggcttg attcattttg caaaatttcc | 420 |
| aggatattga caacgttaac ttaataatat cttgaaatat taaagctatt atgattaggg | 480 |
| gtgcaaatgg accgagttgg ttcggtttat atcaaaatca aaccaaacca actatatcgg | 540 |
| tttggattgg ttcggttttg ccgggttttc agcatttct ggtttttttt tgttagatg | 600 |
| aatattattt taatcttact ttgtcaaatt tttgataagt aaatatatgt gttagtaaaa | 660 |
| attaattttt tttacaaaca tatgatctat taaaatattc ttataggaga attttcttaa | 720 |
| taacacatga tatttattta ttttagtcgt ttgactaatt tttcgttgat gtacactttc | 780 |
| aaagttaacc aaatttagta attaagtata aaaatcaata tgatacctaa ataatgatat | 840 |
| gttctattta atttttaaatt atcgaaattt cacttcaaat tcgaaaaaga tatataagaa | 900 |
| ttttgatagg ttttgacata tgaatatgga agaacaaaga gattgacgca ttttagtaac | 960 |
| acttgataag aaagtgatcg tacaaccaat tatttaaagt taataaaaat ggagcacttc | 1020 |
| atatttaacg aaatattaca tgccagaaga gtcgcaaata tttctagata ttttttaaag | 1080 |
| aaaattctat aaaagtcttt aaaggcatat atataaaaac tatatattta tattttggtt | 1140 |
| tggttcgaat ttgttttact caataccaaa ctaaattaga ccaaatataa ttgagatttt | 1200 |
| taatcgcggc ccatgatcac accggtgtaa ttcactggcc gtcgttttac aacgtcgtga | 1260 |
| ctgggaaaac cctggcgtta cccaacttaa tcgccttgca gcacatcccc ctttcgccag | 1320 |
| ctggcgtaat agcgaagagg cccgcaccga tcgcccttcc caacagttgc gcagcctgaa | 1380 |
| tggcgaatgg cgcctgatgc ggtatttct ccttacgcat ctgtgcggta tttcacaccg | 1440 |
| catatggtgc actctcagta caatctgctc tgatgccgca tagttaagcc agccccgaca | 1500 |
| cccgccaaca cccgctgacg cgccctgacg ggcttgtctg ctcccggcat ccgcttacag | 1560 |
| acaagctgtg accgtctccg ggagctgcat gtgtcagagg ttttcaccgt catcaccgaa | 1620 |
| acgcgcgaga cgaaagggcc tcgtgatacg cctattttta taggttaatg tcatgataat | 1680 |
| aatggtttct tagacgtcag gtggcacttt tcggggaaat gtgcgcggaa cccctatttg | 1740 |

```
tttattttc  taaatacatt  caaatatgta  tccgctcatg  agacaataac  cctgataaat   1800
gcttcaataa  tattgaaaaa  ggaagagtat  gagtattcaa  catttccgtg  tcgcccttat   1860 tcccttttt   gcggcatttt  gccttcctgt  ttttgctcac  ccagaaacgc  tggtgaaagt   1920
aaaagatgct  gaagatcagt  tgggtgcacg  agtgggttac  atcgaactgg  atctcaacag   1980
cggtaagatc  cttgagagtt  ttcgccccga  agaacgtttt  ccaatgatga  gcacttttaa   2040
agttctgcta  tgtggcgcgg  tattatcccg  tattgacgcc  gggcaagagc  aactcggtcg   2100
ccgcatacac  tattctcaga  atgacttggt  tgagtactca  ccagtcacag  aaaagcatct   2160
tacggatggc  atgacagtaa  gagaattatg  cagtgctgcc  ataaccatga  gtgataacac   2220
tgcggccaac  ttacttctga  caacgatcgg  aggaccgaag  gagctaaccg  ctttttttgca  2280 caacatgggg  gatcatgtaa  ctcgccttga  tcgttgggaa  ccggagctga  atgaagccat   2340
accaaacgac  gagcgtgaca  ccacgatgcc  tgtagcaatg  gcaacaacgt  tgcgcaaact   2400
attaactggc  gaactactta  ctctagcttc  ccggcaacaa  ttaatagact  ggatggaggc   2460
ggataaagtt  gcaggaccac  ttctgcgctc  ggcccttccg  gctggctggt  ttattgctga   2520
taaatctgga  gccggtgagc  gtgggtctcg  cggtatcatt  gcagcactgg  ggccagatgg   2580
taagccctcc  cgtatcgtag  ttatctacac  gacggggagt  caggcaacta  tggatgaacg   2640
aaatagacag  atcgctgaga  taggtgcctc  actgattaag  cattggtaac  tgtcagacca   2700
agtttactca  tatatacttt  agattgattt  aaaacttcat  ttttaattta  aaaggatcta   2760
ggtgaagatc  cttttgata   atctcatgac  caaaatccct  taacgtgagt  tttcgttcca   2820
ctgagcgtca  gaccccgtag  aaaagatcaa  aggatcttct  tgagatcctt  tttttctgcg   2880
cgtaatctgc  tgcttgcaaa  caaaaaaacc  accgctacca  gcggtggttt  gtttgccgga   2940
tcaagagcta  ccaactcttt  ttccgaaggt  aactggcttc  agcagagcgc  agataccaaa   3000
tactgtcctt  ctagtgtagc  cgtagttagg  ccaccacttc  aagaactctg  tagcaccgcc   3060
tacatacctc  gctctgctaa  tcctgttacc  agtggctgct  gccagtggcg  ataagtcgtg   3120
tcttaccggg  ttggactcaa  gacgatagtt  accggataag  gcgcagcggt  cgggctgaac   3180
ggggggttcg  tgcacacagc  ccagcttgga  gcgaacgacc  tacaccgaac  tgagatacct   3240
acagcgtgag  ctatgagaaa  gcgccacgct  tcccgaaggg  agaaaggcgg  acaggtatcc   3300
ggtaagcggc  agggtcggaa  caggagagcg  cacgagggag  cttccagggg  gaaacgcctg   3360
gtatctttat  agtcctgtcg  ggtttcgcca  cctctgactt  gagcgtcgat  ttttgtgatg   3420
ctcgtcaggg  gggcggagcc  tatggaaaaa  cgccagcaac  gcggcctttt  tacggttcct   3480
ggccttttgc  tggccttttg  ctcacatgtt  ctttcctgcg  ttatcccctg  attctgtgga   3540
taaccgtatt  accgcctttg  agtgagctga  taccgctcgc  cgcagccgaa  cgaccgagcg   3600
cagcgagtca  gtgagcgagg  aagcgtgcgc  agcgtgcgca  gcgtgcgcag  cggaagagcg   3660
cccaatacgc  aaaccgcctc  tccccgcgcg  ttggccgatt  cattaatgca  gctggcacga   3720
caggtttccc  gactggaaag  cgggcagtga  gcgcaacgca  attaatgtga  gttagctcac   3780
tcattaggca  ccccaggctt  tacactttat  gcttccggct  cgtatgttgt  gtggaattgt   3840
gagcggataa  caatttcaca  caggaaacag  ctatgaccat  gattacgcca  agctacaccg   3900
gtgactagaa  acccggccgc  tatgtattac  accataatat  cgcactcagt  ctttcatcta   3960
cggcaatgta  ccagctgata  taatcagtta  ttgaaatatt  tctgaattta  aacttgcatc   4020
aataaattta  tgttttgct   tggactataa  tacctgactt  gttatttat   caataaatat   4080 ttaaactata  tttctttcaa  gatatcattc  tttacaagta  tacgtgttta  aattgaatac   4140
```

```
cataaatttt tattttttcaa atacatgtaa aattatgaaa tgggagtggt ggcgaccgca      4200
agcacacttc aattcctata acggaccaaa tcgcaaaaat tataataaca tattatttca      4260
tcctggatta aaagaaagtc accggggatt attttgtgac gccgattaca tacggcgaca      4320
ataaagacat tggaaatcgt agtacatatt ggaatacact gattatatta gtgatgaata      4380
catactttaa tatccttacg taggatcaac atatcttgtt acaatcggac acttttgctt      4440
catcccgcta acacctctgc accttagacc aagcgcttcc acaaggaact gagagccata      4500
gcccacctca ccttgggttc ctttggccgc ctgtctttct gaaagagagc cttgcccacc      4560
gcaactattt caacacagat aggatcaacc cgggatggcg ctaagaagct attgccgccg      4620
atctgggcgc ctatctagtc aagggcgaat tccagcacac tggcggccgt tactagtgga      4680
tccgagctct aagctcataa gctcataagc tcaagctcag ggtacctcag atctgggtaa      4740
ctggcctaac tggccttgga ggagctggca actcaaaatc cctttgccaa aaaccaacat      4800
catgccatcc accatgcttg tatccagctg cgcgcaatgt accccgggct gtgtatccca      4860
aagcctcatg caacctaaca gatggatcgt ttggaaggcc tataacagca accacagact      4920
taaaaccttg cgcctccata gacttaagca aatgtgtgta caatgtggat cctaggccca      4980
acctttgatg cctatgtgac acgtaaacag tactctcaac tgtccaatcg taagcgttcc      5040
tagccttcca gggcccagcg taagcaatac cagcccacaac ccctcaacc tcagcaacca      5100 accaagggta tctatcttgc aacctctcta gatcatcaat ccactcttgt ggtgtttgtg      5160
gctctgtcct aaagttcact gtagacgtct caatgtaatg gttaacgata tcacaaaccg      5220
cggccatatc agctgctgta gctggcctaa tctcaactgg tctcctctcc ggagaagcca      5280
tggttggatc cttacctgtt aatcagaaaa actcagatta atcgacaaat tcgatcgcac      5340
aaactagaaa ctaacaccag atctagatag aaatcacaaa tcgaagagta attattcgac      5400
aaaactcaaa ttatttgaac aaatcggatg atatttatga aaccctaatc gagaattaag      5460
atgatatcta acgatcaaac ccagaaaatc gtcttcgatc taagattaac agaatctaaa      5520
ccaaagaaca tatacgaaat tgggatcgaa cgaaaacaaa atcgaagatt ttgagagaat      5580
aaggaacaca gaaatttacc ttgatcacgg tagagagaat tgagagaaag ttttttaagat     5640 tttgagaaat tgaaatctga attgtgaaga agaagctttg ggtattgttt tatagaagaa      5700
gaagaagaaa agacgaggac gactaggtca cgagaaagct aaggcggtga agcaatagct      5760
aataataaaa tgcacgtgt attgagcgtt gtttacacgc aaagttgttt ttggctaatt       5820
gccttatttt taggttgagg aaaagtattt gtgctttgag ttgataaaca cgactcgtgt      5880
gtgccggctg caaccacttt gacgccgttt attactgact cgtcgacaac cacaatttct      5940
aacggtcgtc ataagatcca gccgttgaga tttaacgatc gttacgattt atattttttt      6000
agcattatcg ttttatttttt taaatatacg gtggagctga aaattggcaa taattgaacc      6060
gtgggtccca ctgcattgaa gcgtatttcg tattttctag aattcttcgt gctttatttc      6120
ttttcctttt tgttttttttt tgccatttat ctaatgcaag tgggcttata aaatcagtga      6180
atttcttgga aaagtaactt ctttatcgta taacatattg tgaaattatc catttctttt      6240 aatttttttag tgttattgga tatttttgta tgattattga tttgcatagg ataatgactt      6300
ttgtatcaag ttggtgaaca agtctcgtta aaaaggcaa gtggtttggt gactcgatttt      6360 attcttgtta tttaattcat atatcaatgg atcttatttg gggcctggtc catatttaac      6420
actcgtgttc agtccaatga ccaataatat ttttcatta ataacaatgt aacaagaatg       6480
atacacaaaa cattctttga ataagttcgc tatgaagaag ggaacttatc cggtcctaga      6540
```

```
tcatcagttc atacaaacct ccatagagtt caacatctta aacaagaata tcctgatccg    6600
ttgacctgca ggcggggttt aaacatttaa atttaattaa gcggccgcgg ccggccgagc    6660
ataattttta ttaatgtact aaattactgt tttgttaaat gcaattttgc tttctcggga    6720
ttttaatatc aaaatctatt tagaaataca caatattttg ttgcaggctt gctggagaat    6780
cgatctgcta tcataaaaat tacaaaaaaa ttttatttgc ctcaattatt ttaggattgg    6840
tattaaggac gcttaaatta tttgtcgggt cactacgcat cattgtgatt gagaagatca    6900
gcgatacgaa atattcgtag tactatcgcg ataatttatt tgaaaattca tatgaaaagc    6960
aaacgttaca tgaattgatg aaacaataca aagacagata aagccacgca catttaggat    7020
attggccgag attactgaat attgagtaag atcacggaat ttctgacagg agcatgtctt    7080
caattcagcc caaatggcag ttgaaatact caaaccgccc catatgcagg agcggatcat    7140
tcattgtttg tttggttgcc tttgccaaca tgggagtcca aggtttggtg accgcatgcg    7200
agctctcaca ggtaggtctt gcggcaatcc acggcgcgca cggtctcctt caggctcata    7260
ttatcgcggt gatcggtcac atccttgctc agcttcacgt ggtagctcat gtggtggtac    7320
tcgggcacgt gcacggggcc gccgccgatg ggggtattca tctgggtgtg atcggccacg    7380
atgaaatcgc ccttgctgcc ggtgatctcg tggcagatct tgaaggcgct cttcaggccg    7440
tgattggcct gatcgcccca gatgtacagg cagtgggggg tgaaattgaa ctccagattc    7500
ttgcccagca cgtggccatc cttcttgaag ccctggccat tcagcttcac gcgattgtac    7560
acgctgccat tctcgaaggt cacctcggcg cgggtcttga aattgccatc gcctcgaag    7620 gtgatggtgc gctcctgcac gtagccatcg gcatgcagc tcttgtagaa atccttcagc    7680
tcggggccgt acttggcgaa gcactgggcg ccgtaggtca gggtggtcac cagggtgctc    7740
cagggcacgg gcacatcgcc ggtggtgcag atgaactggg catccacctt gcccacgctg    7800
gcatcgccgt agcccttgcc gcggatgctg aaggtgtggc catccacatt gccctccatc    7860
tccaccacgt aggggatctt gccgtggaac agcagggcgc cgctggagcc catggagatc    7920
tacaaactta caaatttctc tgaagttgta tcctcagtac ttcaaagaaa atagcttaca    7980
ccaaattttt tcttgttttc acaaatgccg aacttggttc cttatatagg aaaactcaag    8040
ggcaaaaatg acacggaaaa atataaaagg ataagtagtg ggggataaga ttccttgtg    8100 ataaggttac tttccgccct tacatttcc accttacatg tgtcctctat gtctctttca    8160
caatcaccga cctatcttc ttcttttcat tgttgtcgtc agtgcttacg tcttcaagat    8220
tcttttcttc gcctggttct tcttttcaa tttctacgta ttcttcttcg tattctggca    8280
gtataggatc ttgtatctgt acattcttca tttttgaaca taggttgcat atgtgccgca    8340
tattgatctg cttcttgctg agcttacata atacttccat agttttttccc gtaaacattg    8400 gattcttgat gctacatctt ggataattac cttctgggtt tagcggcc                  8448
```

<210> SEQ ID NO 3
<211> LENGTH: 24
<212> TYPE: DNA
<213> ORGANISM: Artificial sequence
<220> FEATURE:
<223> OTHER INFORMATION: Forward primer for YFP

<400> SEQUENCE: 3
tgttccacgg caagatcccc tacg    24

<210> SEQ ID NO 4
<211> LENGTH: 24

-continued

```
<212> TYPE: DNA
<213> ORGANISM: Artificial sequence
<220> FEATURE:
<223> OTHER INFORMATION: Reverse primer for YFP

<400> SEQUENCE: 4
tattcatctg ggtgtgatcg gcca                                              24

<210> SEQ ID NO 5
<211> LENGTH: 24
<212> TYPE: DNA
<213> ORGANISM: Artificial sequence
<220> FEATURE:
<223> OTHER INFORMATION: Forward primer for PAT

<400> SEQUENCE: 5
ggagaggaga ccagttgaga ttag                                              24

<210> SEQ ID NO 6
<211> LENGTH: 24
<212> TYPE: DNA
<213> ORGANISM: Artificial sequence
<220> FEATURE:
<223> OTHER INFORMATION: Reverse primer for PAT

<400> SEQUENCE: 6
agatctgggt aactggccta actg                                              24
```